United States Patent
Toothman

(10) Patent No.: US 10,617,700 B1
(45) Date of Patent: *Apr. 14, 2020

(54) VITAMIN SUPPLEMENT COMPOSITIONS WITH ENHANCED BIOAVAILABILITY

(71) Applicant: Michelle Ann Toothman, Alexandria, VA (US)

(72) Inventor: Michelle Ann Toothman, Alexandria, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/253,508

(22) Filed: Jan. 22, 2019

Related U.S. Application Data

(63) Continuation-in-part of application No. 16/055,817, filed on Aug. 6, 2018, now abandoned, which is a continuation-in-part of application No. 15/255,669, filed on Sep. 2, 2016, now Pat. No. 10,039,765, which is a continuation-in-part of application No. 15/054,833, filed on Feb. 26, 2016, now Pat. No. 10,039,805.

(51) Int. Cl.
| | | |
|---|---|---|
| *A61K 31/675* | (2006.01) | |
| *A61K 31/519* | (2006.01) | |
| *A61K 31/714* | (2006.01) | |
| *A61P 3/02* | (2006.01) | |
| *A61K 9/00* | (2006.01) | |
| *A23L 33/15* | (2016.01) | |

(52) U.S. Cl.
CPC .......... *A61K 31/675* (2013.01); *A61K 31/519* (2013.01); *A61K 31/714* (2013.01); *A61P 3/02* (2018.01); *A23L 33/15* (2016.08); *A23V 2002/00* (2013.01); *A23V 2200/30* (2013.01); *A23V 2250/706* (2013.01); *A23V 2250/7052* (2013.01); *A23V 2250/7058* (2013.01); *A61K 9/0056* (2013.01)

(58) Field of Classification Search
CPC .. A61K 31/675; A61K 31/519; A61K 31/714; A61K 9/0056; A61P 3/02; A23L 33/15; A23V 2002/00; A23V 2200/30; A23V 2250/7052; A23V 2250/7058; A23V 2250/706

See application file for complete search history.

(56) References Cited

U.S. PATENT DOCUMENTS

| | | | |
|---|---|---|---|
| 4,973,467 A | 11/1990 | Sahley | |
| 5,332,579 A | 7/1994 | Umbdenstock | |
| 5,468,506 A | 11/1995 | Andon | |
| 5,494,678 A | 2/1996 | Paradissis et al. | |
| 5,686,491 A | 11/1997 | Sherwood | |
| 6,190,724 B1 | 2/2001 | Sawatzki et al. | |
| 6,361,800 B1 | 3/2002 | Cooper et al. | |
| 6,365,177 B1 | 4/2002 | Shahadeh | |
| 6,369,042 B1 | 4/2002 | Oberthur et al. | |
| 6,451,341 B1 | 9/2002 | Slaga et al. | |
| 6,488,956 B1 | 12/2002 | Paradissis et al. | |
| 6,589,576 B2 | 7/2003 | Borschel et al. | |
| 6,605,646 B2 | 8/2003 | Herbert | |
| 6,613,367 B1* | 9/2003 | Wells ................. | A61K 31/4415 426/590 |
| 6,645,543 B2 | 11/2003 | Gohman et al. | |
| 6,777,391 B1 | 8/2004 | Kratky et al. | |
| 6,863,918 B2 | 3/2005 | Bindels et al. | |
| 6,881,419 B2 | 4/2005 | Lovett | |
| 6,913,778 B2* | 7/2005 | Kuhlman ............ | A23C 9/1512 426/583 |
| 7,070,825 B2 | 7/2006 | Ndife et al. | |
| 8,197,855 B2 | 6/2012 | Giordano et al. | |
| 8,263,667 B2 | 9/2012 | Squashic et al. | |
| 8,377,430 B2* | 2/2013 | Donnet-Hughes ......................... | A61K 35/741 424/93.1 |
| 8,592,392 B2 | 11/2013 | Prasad et al. | |
| 10,039,765 B1 | 8/2018 | Toothman | |
| 10,039,805 B1 | 8/2018 | Toothman | |
| 2004/0106561 A1 | 6/2004 | Kelly | |
| 2005/0032741 A1 | 2/2005 | Venkataraman | |
| 2005/0214383 A1 | 9/2005 | Bubnis et al. | |
| 2006/0127499 A1 | 6/2006 | Lazarev et al. | |
| 2008/0145475 A1 | 6/2008 | Flatt et al. | |

(Continued)

FOREIGN PATENT DOCUMENTS

| | | |
|---|---|---|
| WO | WO 2013/138906 | 9/2013 |
| WO | WO 2013138906 A1 * | 9/2013 |

OTHER PUBLICATIONS

New et al. ("The Use of B Vitamins for Cutaneous Ulcerations Mimicking Pyoderma Gangrenosum in Patients With MTHFR Polymorphism" in the Arch Dermatol. 2011, 147(4).*
EFSA Journal, 2013, 11 (10):3358; opinion of the efsa.*
Greenberg et al. ("Folic Acid Supplementation and Pregnancy: More Than Just Neural Tube Defect Prevention" in Reviews in Obstetrics and Gynecology, vol. 4, 2011).
Office Action for U.S. Appl. No. 15/255,669 dated Mar. 21, 2017.
Office Action for U.S. Appl. No. 15/255,669 dated Oct. 17, 2017.

(Continued)

*Primary Examiner* — Blessing M Fubara
(74) *Attorney, Agent, or Firm* — King & Partners, PLLC

(57) ABSTRACT

A vitamin supplement composition that includes a complex with enhanced bioavailability having a vitamin B complex, wherein the vitamin B complex includes: (a) a first vitamin, wherein the first vitamin comprises a form of vitamin $B_6$; (b) a second vitamin, wherein the second vitamin comprises a form of vitamin $B_9$; (c) a third vitamin, wherein the third vitamin comprises a form of vitamin $B_{12}$; and (d) wherein the first vitamin, the second vitamin, and the third vitamin cooperate synergistically to enhance bioavailability of the same. The present invention further includes a method of administering a vitamin supplement composition to an individual having, for example, MTHFR deficiency.

14 Claims, No Drawings

(56) References Cited

U.S. PATENT DOCUMENTS

2010/0068346 A1  3/2010  Hodges
2014/0323574 A1  10/2014  Yao et al.
2015/0140174 A1  5/2015  Shao et al.
2015/0335052 A1* 11/2015  Sprenger ................ A23L 33/21
                                                    426/61

OTHER PUBLICATIONS

Office Action for U.S. Appl. No. 15/255,669 dated Apr. 5, 2018.
Office Action for U.S. Appl. No. 15/054,833 dated Oct. 18, 2016.
Office Action for U.S. Appl. No. 15/054,833 dated Mar. 20, 2017.
Office Action for U.S. Appl. No. 15/054,833 dated Sep. 25, 2017.
Office Action for U.S. Appl. No. 15/054,833 dated Apr. 3, 2018.

* cited by examiner

VITAMIN SUPPLEMENT COMPOSITIONS WITH ENHANCED BIOAVAILABILITY

CROSS-REFERENCE TO RELATED APPLICATIONS

This application is a continuation-in-part of U.S. application Ser. No. 16/055,817, filed Aug. 6, 2018, entitled "Infant Formulas Having Vitamin Complexes With Enhanced Bioavailability," which is a continuation-in-part of U.S. application Ser. No. 15/255,669, filed Sep. 2, 2016, entitled "Vitamin Supplement Compositions With Enhanced Bioavailability," now U.S. Pat. No. 10,039,765, and U.S. application Ser. No. 15/054,833, filed Feb. 26, 2016, entitled "Infant Formulas Having Vitamin Complexes With Enhanced Bioavailability," now U.S. Pat. No. 10,039,805, all of which are hereby incorporated herein by reference in their entirety—including all references cited therein.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to vitamin supplement compositions and, more particularly, to novel vitamin supplement compositions that comprise complexes having enhanced bioavailability for maximizing nutritional absorption. While the vitamin supplement compositions of the present invention are suitable for individuals of any age (e.g., an infant, toddler, child, adolescent, adult, elderly, etcetera), they are particularly beneficial for individuals that present genetic or other types of disorders (e.g., known or unknown methylenetetrahydrofolate reductase (MTHFR) CT polymorphism, genetic defects in MTHFR, MTHFR deficiency, etcetera). The vitamin supplement compositions of the present invention are preferably swallowable, chewable, and/or dissolvable and suitable for use in liquid, gel, gummy, tablet, pill, capsule, powder, and/or other conventional supplement forms.

2. Background Art

Vitamin supplements have been known in the art for years and are the subject of a plurality of patents and/or publications, including: U.S. Pat. No. 8,592,392 entitled "Multiple Antioxidant Micronutrients," U.S. Pat. No. 8,263,667 entitled "Nutritional Supplement for Use Under Physiologically Stressful Conditions," U.S. Pat. No. 8,197,855 entitled "Compositions and Methods for Nutrition Supplementation," U.S. Pat. No. 6,881,419 entitled "Vitamin Formulation for Enhancing Bone Strength," U.S. Pat. No. 6,605,646 entitled "Vitamin Supplement Composition," U.S. Pat. No. 6,488,956 entitled "Multi-Vitamin and Mineral Supplements for Women," U.S. Pat. No. 6,451,341 entitled "Time Release Formulation of Vitamins, Minerals and Other Beneficial Supplements," U.S. Pat. No. 6,369,042 entitled "Antioxidative Vitamin B6 Analogs," U.S. Pat. No. 6,361,800 entitled "Multi-Vitamin and Mineral Supplement," U.S. Pat. No. 5,494,678 entitled "Multi-Vitamin and Mineral Supplement for Pregnant Women," U.S. Pat. No. 5,468,506 entitled "Concentrated Bioavailable Calcium Source," U.S. Pat. No. 5,332,579 entitled "Nutritional Supplement for Optimizing Cellular Health," U.S. Pat. No. 4,973,467 entitled "Dietary Supplement for Adults," United States Patent Application Publication No. 2006/0127499 entitled "Vitamin-Mineral Compositions," United States Patent Application Publication No. 2005/0214383 entitled "Multi-Vitamin and Mineral Nutritional Supplements," United States Patent Application Publication No. 2005/0032741 entitled "Vitamin Compositions," and United States Patent Application Publication No. 2004/0106561 entitled "Health Supplement," all of which are hereby incorporated herein by reference in their entirety—including all references cited therein.

U.S. Pat. No. 8,592,392 appears to disclose a method for optimizing the health of humans according to their age and sex. The method comprises administering to said humans a daily dose of a multiple antioxidant micronutrient composition comprising vitamin A (palmitate), beta-carotene (from natural d. salina), vitamin C (calcium ascorbate), vitamin D-3 (cholecalciferol), natural source vitamin E including both d-alpha tocopherol and d-alpha tocopheryl acid succinate, thiamine mononitrate, riboflavin, niacinamide ascorbate, d-calcium pantothenate, pyridoxine hydrochloride, cyanocobalamin, folic acid (folacin), d-biotin, selenium (1-seleno methionine), chromium picolinate, zinc glycinate, calcium citrate, and magnesium citrate. For persons over the age of about 51, the composition preferably further comprises one or more of co-enzyme $Q_{10}$, N-acetyl cysteine, and alpha lipoic acid. Preferably, also, vitamin D is added for women over the age of about 36.

U.S. Pat. No. 8,263,667 appears to disclose a nutritional supplement for use in physiologically stressful conditions. The nutritional supplement may include one or more of vitamin A, vitamin E, vitamin D3, vitamin C, vitamin B1, riboflavin, niacin, folic acid, vitamin $B_6$, biotin, pantothenic acid, vitamin $B_{12}$, magnesium, zinc, selenium, chromium, copper, iron, alpha lipoic acid, lutein and lycopene.

U.S. Pat. No. 8,197,855 appears to disclose compositions that may be swallowable, chewable or dissolvable, comprising various vitamins and minerals, and in a specific embodiment comprising vitamin A, beta carotene, B-complex vitamins, vitamin C, vitamin D3, vitamin E, iron, magnesium and zinc, and methods for using these compositions for nutritional supplementation in subjects undergoing physiologically stressful events, such as, for example and without limitation, pregnancy, lactation or any disease state.

U.S. Pat. No. 6,881,419 appears to disclose a method and composition for dietary vitamin supplementation utilizing a form and dosage of vitamins and minerals for enhanced calcium absorption. The method includes the steps of providing a pharmaceutically acceptable composition including calcium citrate, and supplementing the daily dietary regimen of a subject with calcium citrate within the range of approximately 100 mg calcium to approximately 2,000 mg calcium, and preferably 1,000 mg calcium. The chewable form of the supplement provided herein facilitates absorption of calcium in the teeth and bones of a subject, for enhanced physiological and psychological benefits. The supplement is especially beneficial for subjects experiencing osteoporosis, arthritis, demineralization of teeth and bones, bodily pain and lack of energy, as well as for the prevention of these ailments.

U.S. Pat. No. 6,605,646 appears to disclose a vitamin $B_{12}$ supplement composition comprising vitamin $B_{12}$ with and/or without added folic acid that is essentially free of antioxidants, such as vitamin C, as well as iron. Also disclosed are methods of using this vitamin composition to prevent brain and nervous system damage, such as peripheral nerve damage, as well as pernicious anemia, such as where such anemia is caused by a deficiency of vitamin $B_{12}$ deficiency.

U.S. Pat. No. 6,488,956 appears to disclose multi-vitamin and mineral supplements for administration to non-lactating women, which comprise specific regimens of vitamins and minerals tailored to meet the physiological needs of said women. Methods are disclosed for optimizing the health of women by providing multi-vitamin and mineral supplements which are specifically tailored to achieve optimal regulation of growth, maintenance and repair of body tissue during specific stages of life with minimal side effects. Methods are further disclosed for formulating a multi-vitamin and mineral supplement that optimize the health of a woman and which comprise identifying life stages which correlate to specific nutritional requirements as a result of varying physiological conditions during a lifetime and selecting specific types and optimal amounts of vitamins and minerals for said life stages.

U.S. Pat. No. 6,451,341 appears to disclose a formulation of vitamins, minerals and other beneficial supplements which has been demonstrated to be cancer-protective. It is believed that the formulations of the present invention will also protect against cardiovascular disorders, extend longevity as well as to facilitate immunological integrity in humans. More specifically, the invention is directed to a formulation and methods of manufacturing and administering a formulation containing vitamins and minerals in association with antioxidants, fish oils, enzymes, and amino acids. The formulations of the present invention provide synergistic relationships which have not previously been reported. As a preferred embodiment, the formulations of the present invention are manufactured as a sustained-release tableted dietary supplement and are intended as daily supplements.

U.S. Pat. No. 6,369,042 appears to disclose novel antioxidative Vitamin $B_6$ analogs and their use in the cosmetic, dermatological, pharmaceutical and/or nutritional fields. Analogs can be provided in suitable formulations intended in particular for caring for the skin, make up for the skin, protection from the sun of the skin, as well as for the treatment of diseases of the skin and bone, and viral, parasitic and fungal infections.

U.S. Pat. No. 6,361,800 appears to disclose a multi-vitamin and mineral supplement which supplies the right amount of the right micronutrients at the right time to assure adequate intake of micronutrients needed for disease prevention and protection against nutritional losses and deficiencies due to lifestyle factors and common inadequate dietary patterns. The multi-vitamin and mineral supplement is comprised of vitamin A, vitamin C, vitamin D, vitamin E, vitamin K, vitamin $B_1$, vitamin $B_2$, niacinamide, vitamin $B_6$, vitamin $B_{12}$, biotin, pantothenic acid, iron, phosphorus, iodine, magnesium, zinc, selenium, copper, chromium, potassium, choline, lycopene, and co-enzyme Q-10.

U.S. Pat. No. 5,494,678 appears to disclose multi-vitamin and mineral supplements for administration to a pregnant woman during her first, second, and third trimesters of pregnancy comprising specific regimens of a pharmaceutically acceptable calcium compound, vitamin D, folic acid, vitamin $B_{12}$, vitamin $B_6$, and vitamin $B_1$. The prenatal supplements are specifically tailored to maximize fetal development and maternal health during each trimester of pregnancy.

U.S. Pat. No. 5,468,506 appears to disclose sweetener supplement compositions which provide a bioavailable source of calcium containing: (a) soluble calcium; (b) an edible acid component comprising a mixture of citric acid and malic acid wherein said mixture has a weight ratio of citric acid to malic acid of from about 90:10 to about 10:90; and (c) sugar; in which the weight ratio of the edible acid component to the soluble calcium is from about 3:1 to about 17:1; sugar comprises at least 15%, on a dry weight basis, fructose and the weight ratio of sugar to edible acid component is from about 1:1 to about 40:1.

U.S. Pat. No. 5,332,579 appears to disclose a nutritional supplement, functioning as a food for special dietary use, that enhances diets and assists persons recovering from addiction to health damaging substances. Since cellular damage and deficiencies occur and continue to exist even after the person has stopped abusing the substances, use of the nutritional supplement, which contains a variety of minerals, vitamins, herbs, amino acids, and other substances and nutrients, should be continuous. The nutritional supplement consists of a mixture of nutrients which cooperate synergistically in enhancing cellular metabolic pathways and assists in normalization of cellular functions and optimization of cellular health.

U.S. Pat. No. 4,973,467 appears to disclose a dietary supplement is provided for adults, consisting essentially of GABA (gamma-aminobutyric acid), L-tyrosine, Siberian ginseng, and vitamin $B_6$.

United States Patent Application Publication No. 2006/0127499 appears to disclose compositions of vitamins and minerals used in the prevention and treatment of vitamin and mineral deficiency. These compositions provide a minimization of the intake dosage of vitamins and minerals while still meeting the nutritional daily requirements for these vitamins and minerals. At the same time, these compositions are easier to manufacture, have an improved prolonged shelf-life, and are easy and convenient to use. These compositions comprise 3 to 5 dose formulations that are ingested separately. Each dose formulation contains vitamins and minerals that are compatible with each other regarding systemic absorption and storage shelf-life.

United States Patent Application Publication No. 2005/0214383 appears to disclose a nutritional supplement which includes micronutrients to facilitate reduction of cholesterol, and/or reduction of homocystein and/or reduction of low-density lipoprotein-cholesterol (LDL-C) oxidation in humans. In one embodiment the supplement is a multi-vitamin, a mineral supplement which includes at least one component known to reduce cholesterol. The invention further provides a method for tableting one fourth to one half of the daily effective dosage of a phytosterol containing nutritional supplement in a practical sized tablet and a method for reducing blood cholesterol in humans.

United States Patent Application Publication No. 2005/0032741 appears to disclose vitamin compositions and methods for the treatment or prevention of conditions associated with hormonal changes in an individual. The vitamin compositions contain calcium, vitamin D, folic acid, vitamin $B_{12}$ and vitamin $B_6$. In a preferred embodiment, the vitamin $B_{12}$ is a hydroxocobalamin.

United States Patent Application Publication No. 2004/0106561 appears to disclose natural products containing phyto-oestrogens, or phyto-oestrogen analogues, which have various beneficial physiological effects in man, and which have a variety of uses, such as to promote good health and as a dietary additive, for example. The invention describes a method of improving the health of a human by administering to the human a health supplementing amount of a phyto-oestrogen selected from genistein, daidzein formononentin and/or biochanin A. A health supplement comprising a health supplementary amount of a phyto-oestrogen selected from genisten daidzein formononentin and/or biochanin A, is also described. Preferably, the supplement also comprises at least one dietary suitable excipient, diluent, carrier or food, and may be in the form of a tablet or capsule, for example. Ideally, the phyto-oestrogen is extracted from red clover or from soya, although any source rich in isoflavones may also be used. The supplement can be used to prevent or ameliorate such conditions as breast cancer, benign breast disease, pre-menstrual syndrome, or symptoms associated with menopause in women, or various types of cancer, and especially for high blood cholesterol levels in all humans, for instance.

While the vitamin supplements disclosed supra have been known in the art for years, issues associated with ingredient absorption, bioavailability, safety, and shelf life remain largely problematic and/or unsolved. As such, there is a genuine demand for novel vitamin supplement compositions that comprise complexes having enhanced bioavailability for maximizing nutritional absorption.

These and other objects of the present invention will become apparent in light of the present specification, claims, chemical structures, chemical formulae, and drawings.

SUMMARY OF THE INVENTION

The present invention is directed to a vitamin supplement composition that comprises a complex with enhanced bioavailability, comprising: (a) a vitamin B complex, wherein the vitamin B complex comprises: (1) a first vitamin, wherein the first vitamin comprises a derivative and/or form of vitamin $B_6$; (2) a second vitamin, wherein the second vitamin comprises a derivative and/or form of vitamin $B_9$; (3) a third vitamin, wherein the third vitamin comprises a derivative and/or form of vitamin $B_{12}$; and (b) wherein the first vitamin, the second vitamin, and the third vitamin cooperate synergistically to enhance bioavailability of the same.

In a preferred embodiment of the present invention, the first vitamin comprises the structure of formula I or nutraceutically acceptable salts or solvates thereof:

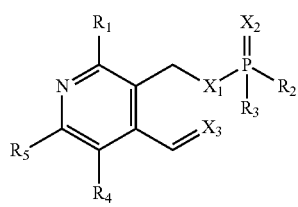

(I)

wherein $R_1$-$R_6$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); wherein at least three of $R_1$-$R_5$ comprise OH; and wherein $X_1$-$X_3$ are each independently selected from the group consisting of N—$R_6$; O; and S.

In another preferred embodiment of the present invention, the first vitamin comprises the structure of formula II or nutraceutically acceptable salts or solvates thereof:

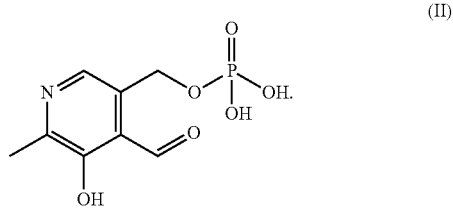 [SMILES: Cc1ncc(COP(=O)(O)O)c(C=O)c1O]

(II)

In yet another preferred embodiment of the present invention, the second vitamin comprises the structure of formula III or nutraceutically acceptable salts or solvates thereof:

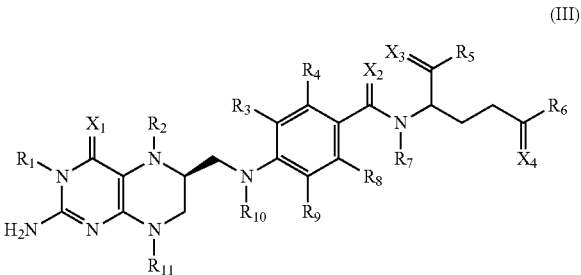

(III)

wherein $R_1$-$R_{12}$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); and wherein $X_1$-$X_4$ are each independently selected from the group consisting of N—$R_{12}$; O; and S.

In another aspect of the present invention, the second vitamin comprises the structure of formula IV or nutraceutically acceptable salts or solvates thereof:

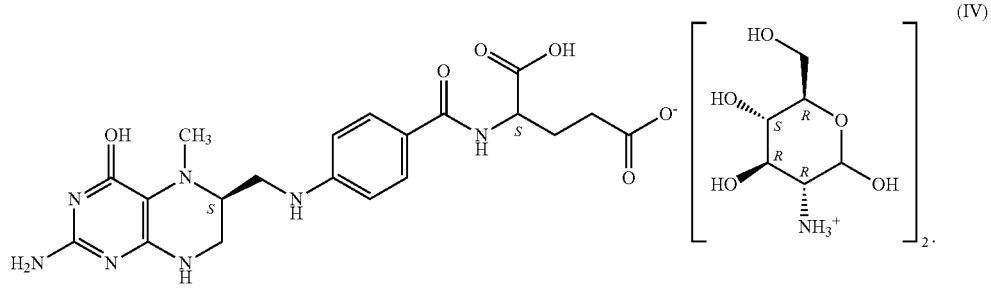

(IV)

In a preferred embodiment of the present invention, the third vitamin comprises the structure of formula V or nutraceutically acceptable salts or solvates thereof:

(V)

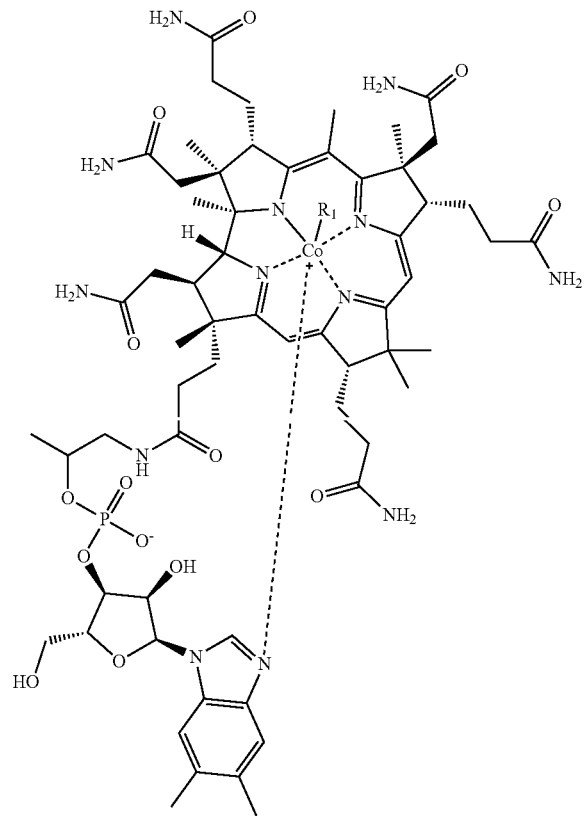

wherein $R_1$ is selected from the group consisting of an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s).

In another preferred embodiment of the present invention, the third vitamin comprises the structure of formula VI or nutraceutically acceptable salts or solvates thereof:

(VI)

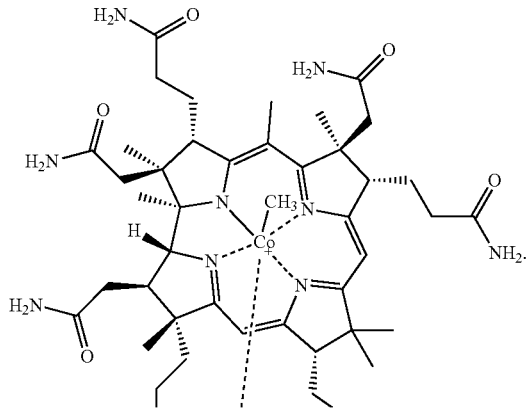

-continued

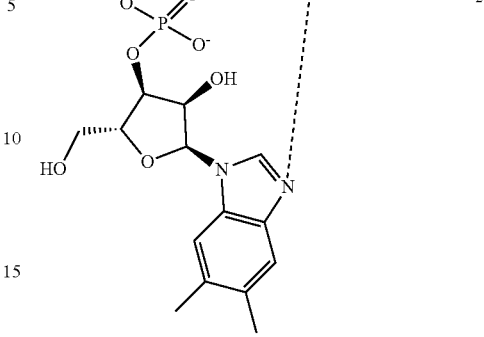

Preferably, the first vitamin comprises [(4-formyl-5-hydroxy-6-methylpyridin-3-yl)methoxy]phosphonic acid, the second vitamin comprises N-[4-[[[(6S)-2-amino-1,4,5,6,7,8-hexahydro-5-methyl-4-oxo-6-pteridinyl]methyl]-amino]benzoyl]-L-glutamic acid, glucosamine salt, and the third vitamin comprises methylcobalamin.

In one embodiment of the present invention, the weight ratio of the first vitamin to the second vitamin to the third vitamin ranges from approximately 300:50:1 to approximately 30:50:1 by weight of the total vitamin B complex, and more preferably is approximately 200:55:1 by weight of the total vitamin B complex.

In a preferred embodiment of the present invention, the vitamin supplement composition further comprises at least one of vitamin A, vitamin C, vitamin D, vitamin E, vitamin K, thiamin, riboflavin, niacin, biotin, pantothenic acid, calcium, iron, iodine, magnesium, zinc, selenium, copper, manganese, chromium, molybdenum, choline, boron, lutein, lycopene, inositol, fruit and/or vegetable blend, and combinations thereof.

In yet another preferred embodiment of the present invention, the vitamin supplement composition further comprises at least one of sweeteners, beeswax, carnuba wax, flavors, emulsifiers, preservatives, colors, glaze, syrups, silica, malic acid, citric acid, magnesium stearate, cellulose, microcrystalline cellulose, croscarmellose sodium, silicon dioxide, maltodextrin, sunflower lecithin, guar gum, sunflower oil, coconut oil, vegetable cellulose, stearic acid, vegetable magnesium stearate, pectin, sodium citrate, dicalcium phosphate, and combinations thereof.

In one preferred embodiment of the present invention, the vitamin supplement composition further comprises one or more fruits and vegetables, preferably in powder form, selected from the group consisting of blueberry, strawberry, raspberry, cherry, elderberry, cranberry, blackberry, bilberry, black currant, pomegranate, broccoli, broccoli sprouts, tomato, carrot, spinach, kale, cauliflower, brussels sprouts, beet, orange, collard greens, lemon, lime, apple, grape, grape seed, pineapple, goji berry, banana, mango, kiwi, onion, cucumber, watermelon, aronia berry, acai berry, cabbage, asparagus, pear, red bell pepper, green bell pepper, plum, parsley, sweet potato, radish sprouts, okra, pumpkin, and combinations thereof.

In yet another preferred embodiment of the present invention, the vitamin supplement composition further comprises a vitamin/mineral selected from the group consisting of vitamin A, thiamin, riboflavin, niacin, pantothenic acid, biotin, vitamin C, choline, vitamin D, vitamin E, vitamin K, calcium, chloride, chromium, copper, fluoride, iodine, iron, magnesium, manganese, molybdenum, nickel, phosphorus, potassium, silicon, selenium, sodium, sulfur, tin, vanadium, zinc, and combinations thereof.

In one preferred embodiment of the present invention, the vitamin supplement composition further comprises an amino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, L-valine, and combinations thereof.

The present invention is also directed to a vitamin supplement composition having a vitamin complex with enhanced bioavailability, comprising: (a) a vitamin B complex, wherein the vitamin B complex comprises: (1) a first vitamin, wherein the first vitamin comprises [(4-formyl-5-hydroxy-6-methylpyridin-3-yl)methoxy]phosphonic acid; (2) a second vitamin, wherein the second vitamin comprises N-[4-[[[(6S)-2-amino-1,4,5,6,7,8-hexahydro-5-methyl-4-oxo-6-pteridinyl]methyl]-amino]benzoyl]-L-glutamic acid, glucosamine salt; and (3) a third vitamin, wherein the third vitamin comprises methylcobalamin, wherein the weight ratio of the first vitamin to the second vitamin to the third vitamin ranges from approximately 300:50:1 to approximately 30:50:1 by weight of the total vitamin B complex; (b) at least five amino acids selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine; (c) minerals; and (d) wherein any remainder comprises adjunct agents.

The present invention is further directed to a method for treating an individual having known or unknown MTHFR CT polymorphism, comprising the step(s) of: orally administering a vitamin B complex, wherein the vitamin B complex comprises: (a) a first vitamin, wherein the first vitamin comprises a form of vitamin $B_6$; (b) a second vitamin, wherein the second vitamin comprises a form of vitamin $B_9$; (c) a third vitamin, wherein the third vitamin comprises a form of vitamin $B_{12}$; and (d) wherein the first vitamin, the second vitamin, and the third vitamin cooperate synergistically to enhance bioavailability of the same.

DETAILED DESCRIPTION OF THE INVENTION

While this invention is susceptible of embodiment in many different forms, there is shown in the structural formulas and described herein in detail several specific embodiments with the understanding that the present disclosure is to be considered as an exemplification of the principles of the invention and is not intended to limit the invention to the embodiments illustrated. It will be understood that the structural formulas disclosed herein are intended to comprise all stereochemcial configurations regardless of graphical representations.

In accordance with the present invention, vitamin supplement compositions are disclosed herein that include vitamins and/or vitamin complexes having enhanced bioavailability for maximizing nutritional absorption. Without being bound by any one particular theory, it is believed that the vitamin supplement compositions of the present invention facilitate enhanced bioavailability by reducing and/or eliminating multi-step biochemical conversions and/or are formulated in such a manner that relevant vitamins or their nutraceutically acceptable salts or solvates are neither compromised and/or adversely affected by other and/or adjunct ingredients. It will be understood that the vitamin supplement compositions of the present invention are preferably swallowable, chewable, and/or dissolvable and suitable for use in liquid, gel, tablet, pill, capsule, powder, and/or other conventional supplement forms.

In a first embodiment of the present invention, the vitamin supplement compositions preferably include a vitamin complex having enhanced bioavailability for maximizing nutritional absorption, relative to vitamin supplement compositions having primarily synthetic and/or conventional vitamers. In accordance with the present invention the vitamin complex preferably includes a first vitamin, wherein the first vitamin comprises a specific vitamer and/or derivative of vitamin $B_6$, a second vitamin, wherein the second vitamin comprises a specific vitamer and/or derivative of vitamin $B_9$, and a third vitamin, wherein the third vitamin comprises a specific vitamer and/or derivative of vitamin $B_{12}$.

For purposes of the present disclosure, the first vitamin preferably comprises the structure of formula I or nutraceutically acceptable salts (e.g., deprotonated derivatives) or solvates thereof:

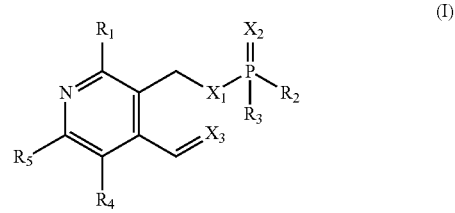

wherein $R_1$-$R_6$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); wherein at least three of $R_1$-$R_5$ comprise OH; and wherein $X_1$-$X_3$ are each independently selected from the group consisting of N—$R_6$; O; and S. In particular, the first vitamin preferably comprises the structure of formula II or nutraceutically acceptable salts or solvates thereof:

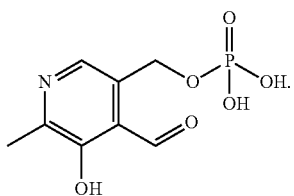

(II)

For purposes of reducing any potential ambiguity associated with the structure of formula II, it will be understood that this structure is a vitamer of vitamin $B_6$ known as [(4-formyl-5-hydroxy-6-methylpyridin-3-yl)methoxy]phosphonic acid and/or pyridoxal-5'-phosphate and is commercially available from Sigma-Aldrich—among other chemical suppliers.

In one embodiment, the second vitamin preferably comprises a folate derivative and/or the structure of formula III or nutraceutically acceptable salts or solvates thereof:

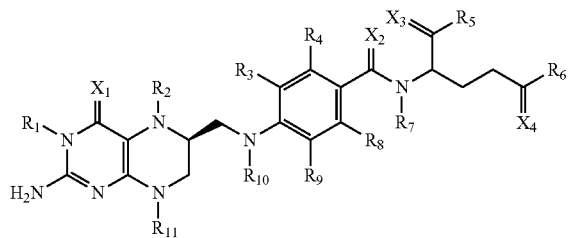

(III)

wherein $R_1$-$R_{12}$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); and wherein $X_1$-$X_4$ are each independently selected from the group consisting of N—$R_{12}$; O; and S. In particular, the second vitamin preferably comprises the structure of formula IV or nutraceutically acceptable salts or solvates thereof:

In accordance with the present invention, the third vitamin preferably comprises the structure of formula V or nutraceutically acceptable salts or solvates thereof:

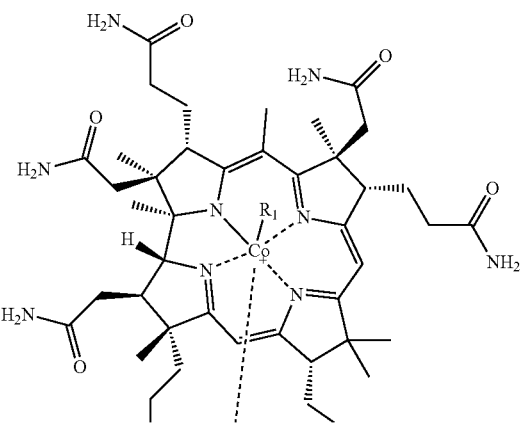

(V)

wherein $R_1$ is selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-

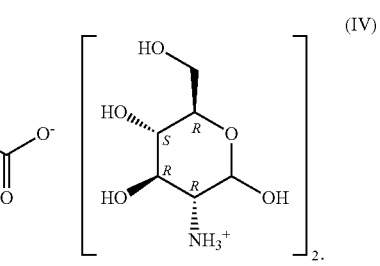

(IV)

For purposes of reducing any potential ambiguity associated with the structure of formula IV, it will be understood that this structure is a vitamer of vitamin $B_9$ known as N-[4-[[[(6S)-2-amino-1,4,5,6,7,8-hexahydro-5-methyl-4-oxo-6-pteridinyl]methyl]-amino]benzoyl]-L-glutamic acid, glucosamine salt.

alkenyl, alcohol, ether, ketone, carboxylic acid, acid halide, acid anhydride, ester, and/or amide group containing approximately 1 to approximately 25 carbon atom(s). In particular, the third vitamin preferably comprises the structure of formula V or nutraceutically acceptable salts or solvates thereof:

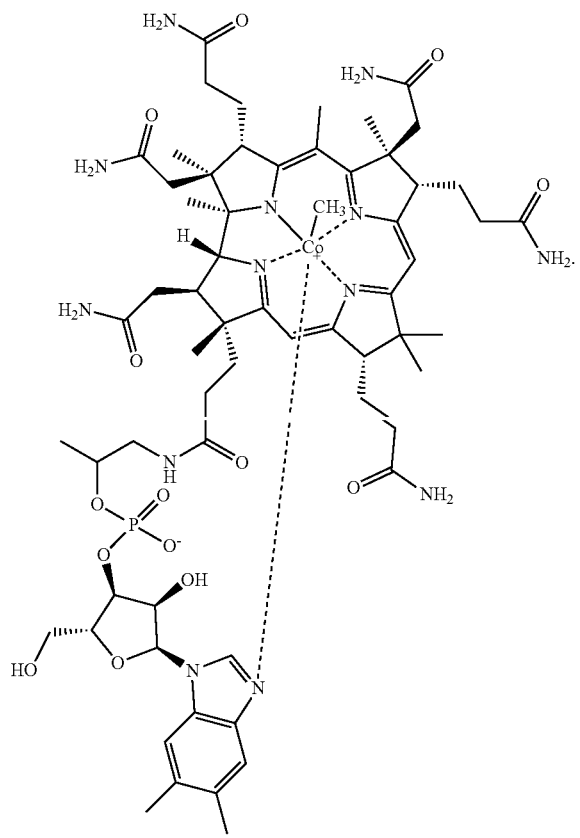

(VI)

For purposes of reducing any potential ambiguity associated with the structure of formula VI, it will be understood that this structure is a vitamer of vitamin $B_{12}$ known as methylcobalamin and is commercially available from Sigma-Aldrich—among other chemical suppliers.

The weight ratio of the first vitamin to the second vitamin to the third vitamin preferably ranges from approximately 300:50:1 to approximately 100:20:1 by weight of the total vitamin B complex, and more preferably ranges from approximately 250:75:1 to approximately 30:50:1 by weight of the total vitamin B complex. In one embodiment, the weight ratio of the first vitamin to the second vitamin to the third vitamin is approximately 200:55:1 by weight of the vitamin B complex.

In one embodiment of the present invention, the vitamin supplement compositions optionally include animal protein and/or plant protein. Suitable examples of proteins include, for example, egg protein, milk protein, whey protein, whey protein concentrate, whey protein isolate, whey protein hydrolysate, casein protein, hydrolyzed protein, soy protein, rice protein, pea protein, quinoa protein, oat protein, and/or cranberry protein.

In another embodiment of the present invention, the vitamin supplement compositions optionally include a saturated fat, a trans fat, a monounsaturated fat, and/or a polyunsaturated fat—especially including omega-3 and omega-6 fatty acids. Suitable examples include, but are not limited to, hexadecatrienoic acid, α-linolenic acid, stearidonic acid, eicosatrienoic acid, eicosatetraenoic acid, eicosapentaenoic acid, heneicosapentaenoic acid, docosapentaenoic acid, clupanodonic acid, docosahexaenoic acid, tetracosapentaenoic acid, tetracosahexaenoic acid, linoleic acid, gamma-linolenic acid, calendic acid, eicosadienoic acid, dihomo-gamma-linolenic acid, arachidonic acid, docosadienoic acid, adrenic acid, docosapentaenoic acid, tetracosatetraenoic acid, and/or tetracosapentaenoic acid.

The vitamin supplement compositions of the present invention also optionally include one or more amino acids. Non-limiting examples of amino acids include L and D enantiomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine.

In one embodiment of the present invention, the vitamin supplement compositions also optionally include one or more prebiotics, such as galacto- and fructo-oligosaccharides, also known as oligogalactosyllactose, oligogalactose, oligolactose or trans galactooligosaccharides (TOS).

In accordance with the present invention, the vitamin supplement compositions also optionally include one or more nucleotides (adenosine-5'-monophosphate, cytidine-5'-monophosphate, disodium guanosine-5'-monophosphate, disodium uridine-5'-monophosphate, etcetera).

Preferably, the vitamin supplement compositions of the present invention include additional vitamins and minerals. Examples include vitamin A, other B vitamins, thiamin, riboflavin, niacin, pantothenic acid, biotin, vitamin C, choline, vitamin D, vitamin E, vitamin K, calcium, chloride, chromium, copper, fluoride, iodine, iron (e.g., ferrous gluconate, Ferronyl™) magnesium, manganese, molybdenum, nickel, phosphorus, potassium, silicon, selenium, sodium, sulfur, tin, vanadium, zinc, and combinations thereof.

In one embodiment of the present invention, the vitamin supplement compositions also optionally include one or more enzymes and/or fruits, including, but not limited to, amylase, bromelain, cellulose, lactase, lipase, papain, protease, *actinidia deliciosa* (whole fruit) extract (kiwi), mango (fruit), etcetera.

The vitamin supplement compositions of the present invention may also include one or more of sweeteners, beeswax, carnuba wax, flavors (e.g., cocoa, coffee, fruit flavors, natural and/or artificial flavors, etcetera), emulsifiers, preservatives, colors, glaze, syrups, silica, malic acid, citric acid, magnesium stearate, cellulose, microcrystalline cellulose, croscarmellose sodium, silicon dioxide, maltodextrin, sunflower lecithin, guar gum, sunflower oil, coconut oil, vegetable cellulose, stearic acid, vegetable magnesium stearate, pectin, sodium citrate, dicalcium phosphate, medicaments, herbal additives, spice additives (e.g., turmeric, cumin, ginger, cinnamon), phyto additives, plant additives, additional anti-oxidants, buffers, thickening agents, stabilizers, and/or a solvents.

In one preferred embodiment of the present invention, the vitamin supplement composition further comprises one or more fruits and vegetables, preferably in powder form, selected from the group consisting of blueberry, strawberry, raspberry, cherry, elderberry, cranberry, blackberry, bilberry, black currant, pomegranate, broccoli, broccoli sprouts, tomato, carrot, spinach, kale, cauliflower, brussels sprouts, beet, orange, collard greens, lemon, lime, apple, grape, grape seed, pineapple, goji berry, banana, mango, kiwi, onion, cucumber, watermelon, aronia berry, acai berry, cabbage, asparagus, pear, red bell pepper, green bell pepper, plum, parsley, sweet potato, radish sprouts, okra, pumpkin, and combinations thereof.

In accordance with the present invention, the vitamin supplement composition may further comprise citicoline (also known as CDP-choline, cytidine 5'-diphosphocholine)

and/or nutraceutically acceptable salts or solvates thereof, which is represented by the structure of formula VII provided herein below:

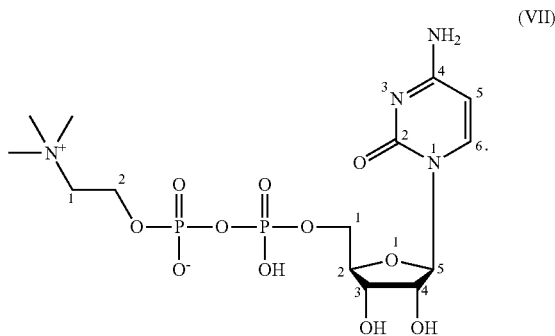

(VII)

In further accordance with the present invention, the vitamin supplement composition may further comprise pantethine and/or nutraceutically acceptable salts or solvates thereof, which is represented by the structure of formula VIII provided herein below:

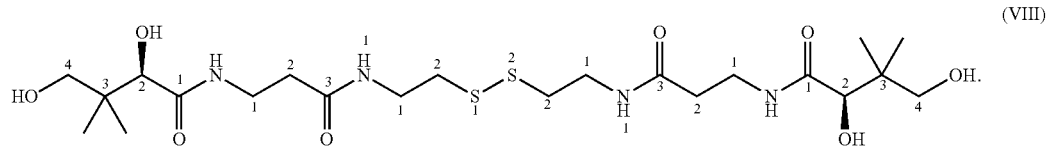 [SMILES: CC(C)(CO)[C@@H](O)C(=O)NCCC(=O)NCCSSCCNC(=O)CCNC(=O)[C@H](O)C(C)(C)CO]

(VIII)

Provided below is a non-limiting example of a multivitamin supplement composition in accordance with the present invention. The vitamins, minerals, and/or ingredients are as follows: Vitamin A Palmitate, Beta Carotene (500-4000 IU), Ascorbic Acid, Calcium Ascorbate, Acerola Cherry fruit extract (20-150 mg), D3 Vegan Cholecalciferol (VitaShine®) (200-800 IU), D-alpha tocopherol acetate, natural mixed tocopherols (5-100 IU), K1 as Phylloquinone and K2 as Menaquinone-7 (Vitamink7™) (6-80 mcg), Thiamine Mononitrate (0.25-5 mg), Riboflavin-5-Phosphate (0.25-5 mg), Niacinamide (2-25 mg), Pyridoxal-5-Phosphate (0.3-50 mg), Quatrefolic®-(6S)-5-methyltetrahydrofolate glucosamine salt (50-800 mcg), Methylcobalamin (1-15 mcg), Biotin (5-300 mcg), Calcium pantothenate (2-15 mg), Calcium citrate malate, Calcium Bisglycinate Chelate (50-500 mg), Ferronyl™ carbonyl iron, Ferrochel® Ferrous Bisglycinate Chelate (2-30 mg), Kelp (10-200 mcg), Magnesium Bisglycinate Chelate (10-200 mg), Zinc Bisglycinate Chelate (2-15 mg), Selenium Glycinate Complex (8-75 mcg), Copper Bisglycinate Chelate (0.1-2 mg), Manganese Bisglycinate Chelate (0.5-3 mg), Chromium Nicotinate Glycinate Chelate (15-150 mcg), Molybdenum Glycinate Chelate (10-100 mcg), Choline Bitartrate (2-200 mg), Bororganic™ Glycine (0.25-150 mcg), Marigold flower extract (10-25 mcg), Tomato extract (10-25 mcg), Inositol (5-50 mcg) and Fruit and vegetable powders (50-300 mg).

Provided below are additional non-limiting examples of vitamin supplement compositions.

| Example 2 (Multivitamin) Amount per serving: | | |
|---|---|---|
| Ingredient Name | Amount | Source |
| Vitamin A Palmitate, Beta Carotene Ascorbic Acid, Calcium Ascorbate, | 500-5000 IU | Parchem |
| Acerola Cherry fruit extract | 20-250 mg | Parchem |
| D3 Vegan Cholecalciferol (VitaShine ®) | 200-800 IU | Vegetology |
| D-alpha tocopherol acetate, natural mixed tocopherols | 5-150 IU | Parchem |
| K1 as Phylloquinone and K2 as Menaquinone-7 (vitamink7 ™) | 5-100 mcg | Parchem/Gnosis USA, Inc. |
| Thiamine Mononitrate | 0.25-7 mg | Parchem |
| Riboflavin-5-Phosphate | 0.25-7 mg | Parchem |
| Niacinamide | 2-25 mg | Parchem |
| Pyridoxal-5-Phosphate | 0.1-50 mg | Parchem |
| Quatrefolic ®-(6S)-5-methyltetrahydrofolate glucosamine salt | 25-1,000 mcg | Gnosis USA, Inc. |
| Methylcobalamin | 1-30 mcg | Parchem |
| Biotin | 5-500 mcg | Parchem |
| Calcium pantothenate | 2-50 mg | Parchem |
| Calcium citrate malate, Calcium Bisglycinate Chelate | 50-700 mg | Albion/Balchem |
| Ferronyl ™ carbonyl iron, Ferrochel ® Ferrous Bisglycinate Chelate | 1-50 mg | Albion/Balchem/Ashland |
| Kelp | 1-500 mcg | Parchem |
| Magnesium Bisglycinate Chelate | 1-500 mg | Albion/Balchem |
| Zinc Bisglycinate Chelate | 1-30 mg | Albion/Balchem |
| Selenium Glycinate Complex | 2-200 mcg | Albion/Balchem |
| Copper Bisglycinate Chelate | 0.1-5 mg | Albion/Balchem |
| Magnesium Bisglycinate Chelate | 0.1-5 mg | Albion/Balchem |

-continued

Example 2 (Multivitamin)
Amount per serving:

| Ingredient Name | Amount | Source |
|---|---|---|
| Chromium Nicotinate Glycinate Chelate | 1-450 mcg | Albion/Balchem |
| Molybdenum Glycinate Chelate | 1-300 mcg | Albion/Balchem |
| Choline Bitartrate | 1-600 mg | Parchem |
| Bororganic ™ Glycine | 0.25-250 mcg | Albion/Balchem |
| Marigold flower extract | 1-50 mcg | Parchem |
| Tomato extract | 1-50 mcg | Parchem |
| Inositol | 1-100 mcg | Parchem |
| Fruit and vegetable powders | 1-500 mg | Powder Pure |

Example 3 (B Complex)
Amount per serving:

| Ingredient Name | Amount | Source |
|---|---|---|
| Pyridoxal-5-Phosphate | .3-50 mg | Parchem |
| Quatrefolic ®-(6S)-5-methyltetrahydrofolate glucosamine salt | 50-800 mcg | Gnosis |
| Methylcobalamin | 1-500 mcg | Parchem |

Example 4 (Calcium)
Amount per serving:

| Ingredient Name | Amount | Source |
|---|---|---|
| Calcium citrate malate, Calcium Bisglycinate Chelate | 50-500 mg | Albion/Balchem |
| D3 Vegan Cholecalciferol (VitaShine ®) | 100-800 IU | Vegetology |
| Magnesium Bisglycinate Chelate | 10-200 mg | Albion/Balchem |
| Zinc Bisglycinate Chelate | 2-15 mg | Albion/Balchem |

Example 5 (Immune Support)
Amount per serving:

| Ingredient Name | Amount | Source |
|---|---|---|
| Ascorbic Acid, Calcium Ascorbate and from acerola fruit extract | 20-150 mg | Parchem |
| Black Elderberry (Sambucus nigra L.) extract (berry) | 10-50 mg | Parchem |
| Zinc Bisglycinate Chelate | 2-15 mg | Albion/Balchem |
| Blackberry, Blueberry, Acerola Cherry | 10-200 mg | Powder Pure |

Example 6 (Brain & Cardiovascular Support)
Amount per serving:

| Ingredient Name | Amount | Source |
|---|---|---|
| Opti3 Omega 3 Complex | 50-1,000 mg | Vegetology |
| D3 Vegan Cholecalciferol (VitaShine ®) | 100-400 IU | Vegetology |

Example 7 (Vitamin D)
Amount per serving:

| Ingredient Name | Amount | Source |
|---|---|---|
| D3 Vegan Cholecalciferol (VitaShine ®) | 200-800 IU | Vegetology |
| Fruit and vegetable powders | 50-300 mg | Powder Pure |

Example 8 (Women's Multivitamin)
Amount per serving:

| Ingredient Name | Amount | Source |
|---|---|---|
| Vitamin C (from Acerola Cherry fruit extract) | 20-150 mg (60 mg) | FutureCeuticals |
| D3 Vegan Cholecalciterol (VitaShine ®) | 5-50 mcg (15 mcg) | The GUT Companies |
| Vitamin E (as d-alpha tocopherol succinate) | 5-100 IU (20 IU) | Marroquin Organics |
| Vitamin K2 (as Menaquinone-7: VitaMK7 ®) | 2-100 mcg (20 mcg) | Gnosis |
| Niacin (as Inositol hexanicotinate and nicotinamide adenine dinucleotide) | 2-25 mg (10 mg) | Parchem |
| Thiamin (as Cocarboxylase) | .25-5 mg (.375 mg) | Parchem |
| Riboflavin (as Riboflavin-5-Phosphate) | .25-5 mg (.425 mg) | Parchem |
| Pantothenic Acid (as Pantethine: Pantesin ®) | 2-15 mg (2.5 mg) | Kyowa Hakko USA |
| Vitamin B6 (as Pyridoxal-5-Phosphate) | 0.5-50 mg (6 mg) | Parchem |
| Quatrefolic ®-(6S)-5-methyltetrahydrofolate glucosamine salt | 50-800 mcg (600 mcg) | Gnosis |
| Vitamin B12 (as Methylcobalamin) | 0.5-15 mcg (8 mcg) | Parchem |
| Biotin (as d-Biotin) | 5-300 mcg (20 mcg) | DSM |
| Iodine (from Kelp) | 10-200 mcg (38 mcg) | Parchem |
| Choline (as Citicoline: Cognizin ®) | 2-600 mg (20 mg) | Kyowa Hakko USA |
| Boron: (as Calcium Fructoborate: FruiteX-B ®) | .25 mcg-2 mg (1 mg) | FutureCeuticals |
| Zinc (as Zinc Bisglycinate Chelate) | 2-15 mg (5 mg) | Albion/Balchem |
| Selenium (as Selenium Glycinate Complex) | 8-75 mcg (10 mcg) | Albion/Balchem |
| Iron (as Ferric Glycinate) | 2-30 mg (8 mg) | Albion/Balchem |
| Magnesium (as Magnesium Bisglycinate Chelate) | 10-200 mg (30 mg) | Albion/Balchem |
| Lutein (from marigolds: FloraGlo ®) | 10 mcg-10 mg (100 mcg) | Kemin/DSM |
| Zeaxanthin (from marigolds: ZeaOne ®) | 10 mcg-10 mg (100 mcg) | Kemin/DSM |
| Fruit and vegetable powder blend: (Strawberry, Raspberry, Blueberry, Tart Cherry, Elderberry, Cranberry, Broccoli, Broccoli Sprouts, Tomato, Carrot, Spinach, Kale) | 20-200 mg (100 mg) | FutureCeuticals |

Example 9 (Men's Multivitamin)
Amount per serving:

| Ingredient Name | Amount | Source |
|---|---|---|
| Vitamin C (from Acerola Cherry fruit extract) | 20-150 mg (60mg) | FutureCeuticals |
| D3 Vegan Cholecalciferol (VitaShine ®) | 5-50 mcg (15 mcg) | The GHT Companies |
| Vitamin E (as d-alpha tocopherol succinate) | 5-100 IU (20 IU) | Marroquin Organics |
| Vitamin K2 (as Menaquinone-7: VitaMK7 ®) | 2-100 mcg (20 mcg) | Gnosis |
| Niacin (as Inositol hexanicotinate and nicotinamide adenine dinucleotide) | 2-25 mg (10 mg) | Parchem |
| Thiamin (as Cocarboxylase) | .25-5 mg (.375 mg) | Parchem |
| Riboflavin (as Riboflavin - 5- Phosphate) | .25-5 mg (.425 mg) | Parchem |
| Pantothenic Acid (as Pantethine: Pantesing | 2-15 mg (2.5 mg) | Kyowa Hakko USA |
| Vitamin B6 (as Pyridoxal-5-Phosphate) | 0.5-50 mg (6 mg) | Parchem |
| Quatrefolic ® - (6S)-5-methyltetrahydrofolate glucosamine salt | 50-800 mcg (400 mcg) | Gnosis |
| Vitamin B12 (as Methylcobalamin) | 0.5-15 mcg (8 mcg) | Parchem |
| Biotin (as d-Biotin) | 5-300 mcg (20 mcg) | DSM |
| Iodine (from Kelp) | 10-200 mcg (38 mcg) | Parchem |
| Choline (as Citicoline: Cognizin ®) | 2-600 mg (20 mg) | Kyowa Hakko USA |
| Boron: (as Calcium Fructoborate: FruiteX-B ®) | .25 mcg-2 mg (500 mcg) | FutureCeuticals |
| Zinc (as Zinc Bisglycinate Chelate) | 2-15 mg (5 mg) | Albion/Balchem |
| Selenium (as Selenium Glycinate Complex) | 8-75 mcg (20 mcg) | Albion/Balchem |
| Magnesium (as Magnesium Bisglycinate Chelate) | 10-200 mg (30 mg) | Albion/Balchem |
| Lutein (from marigolds: FloraGlo ®) | 10 mcg-10 mg (100 mcg) | Kemin/DSM |
| Zeaxanthin (from marigolds: ZeaOne ®) | 10 mcg-10 mg (100 mcg) | Kemin/DSM |
| Lycopene (from tomato extract: redivivo ®) | 10 mcg-10 mg (500 mcg) | Kemin/DSM |
| Fruit and vegetable powder blend: (Strawberry, Raspberry, Blueberry, Tart Cherry, Elderberry, Cranberry, Broccoli, Broccoli Sprouts, Tomato, Carrot, Spinach, Kale) | 20-200 mg (100 mg) | FutureCeuticals |

Example 10 (Children's Multivitamin)
Amount per serving:

| Ingredient Name | Amount | Source |
|---|---|---|
| Vitamin C (from Acerola Cherry fruit extract) | 20-150 mg (40mg) | FutureCeuticals |
| D3 Vegan Cholecalciferol (VitaShine ®) | 5-50 mcg (10 mcg) | The GHT Companies |
| Vitamin E (as d-alpha tocopherol succinate) | 5-100 IU (6 IU) | Marroquin Organics |
| Vitamin K2 (as Menaquinone-7: VitaMK7 ®) | 2-100 mcg (5 mcg) | Gnosis |
| Niacin (as Inositol hexanicotinate and nicotinamide adenine dinucleotide) | 2-25 mg (5 mg) | Parchem |
| Thiamin (as Cocarboxylase) | .25-5 mg (.3 mg) | Parchem |
| Riboflavin (as Riboflavin - 5- Phosphate) | .25-5 mg (.425 mg) | Parchem |
| Pantothenic Acid (as Pantethine: Pantesing | 2-15 mg (2 mg) | Kyowa Hakko USA |
| Vitamin B6 (as Pyridoxal-5-Phosphate) | 0.5-50 mg (1 mg) | Parchem |
| Quatrefolic ® - (6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Biotin (as d-Biotin) | 5-300 mcg (20 mcg) | DSM |
| Iodine (from Kelp) | 10-200 mcg (40 mcg) | Parchem |
| Choline (as Citicoline: Cognizin ®) | 2-600 mg (50 mg) | Kyowa Hakko USA |
| Boron: (as Calcium Fructoborate: FruiteX-B ®) | .25 mcg-2 mg (100 mcg) | FutureCeuticals |
| Zinc (as Zinc Bisglycinate Chelate) | 2-15 mg (4 mg) | Albion/Balchem |

-continued

| Example 10 (Children's Multivitamin) Amount per serving: | | |
|---|---|---|
| Ingredient Name | Amount | Source |
| Iron (as Ferric Glycinate) | 2-30 mg (6 mg) | Albion/Balchem |
| Magnesium (as Magnesium Bisglycinate Chelate) | 10-200 mg (20 mg) | Albion/Balchem |
| Selenium (as Selenium Glycinate Complex) | 8-75 mcg (10 mcg) | Albion/Balchem |
| Lutein (from marigolds: FloraGlo ®) | 10 mcg-10 mg (50 mcg) | Kemin/DSM |
| Zeaxanthin (from marigolds: ZeaOne ®) | 10 mcg-10 mg (50 mcg) | Kemin/DSM |
| Fruit and vegetable powder blend: (Strawberry, Raspberry, Blueberry, Tart Cherry, Elderberry, Cranberry, Broccoli, Broccoli Sprouts, Tomato, Carrot, Spinach, Kale) | 20-200 mg (100 mg) | FutureCeuticals |

| Example 11 (Prenatal Multivitamin) Amount per serving: | | |
|---|---|---|
| Ingredient Name | Amount | Source |
| Vitamin C (as Ascorbic Acid) | 20-150 mg (60mg) | Parchem |
| D3 Vegan Cholecalciferol (VitaShine ®) | 5-50 mcg (20 mcg) | The GHT Companies |
| Vitamin E (as d-alpha tocopherol succinate) | 5-100 IU (10 IU) | Marroquin Organics |
| Vitamin K2 (as Menaquinone-7: VitaMK7 ®) | 2-100 mcg (40 mcg) | Gnosis |
| Niacin (as Inositol hexanicotinate and nicotinamide adenine dinucleotide) | 2-25 mg (10 mg) | Parchem |
| Thiamin (as Cocarboxylase) | .25-5 mg (2 mg) | Parchem |
| Riboflavin (as Riboflavin - 5- Phosphate) | .25-5 mg (1 mg) | Parchem |
| Pantothenic Acid (as Pantethine: Pantesing | 2-15 mg (4 mg) | Kyowa Hakko USA |
| Vitamin B6 (as Pyridoxal-5-Phosphate) | 0.5-50 mg (6 mg) | Parchem |
| Quatrefolic ® - (65)-5-methyltetrahydrofolate glucosamine salt | 50-800 mcg (800 mcg) | Gnosis |
| Vitamin B12 (as Methylcobalamin) | 0.5-15 mcg (8 mcg) | Parchem |
| Biotin (as d-Biotin) | 5-300 mcg (30 mcg) | DSM |
| Iodine (as Potassium Iodide) | 10-200 mcg (150 mcg) | Parchem |
| Choline (as Citicoline: Cognizin ®) | 2-600 mg (50 mg) | Kyowa Hakko USA |
| Boron: (as Calcium Fructoborate: FruiteX-B ®) | .25 mcg-2 mg (1 mg) | FutureCeuticals |
| Zinc (as Zinc Bisglycinate Chelate) | 2-15 mg (10 mg) | Albion/Balchem |
| Selenium (as Selenium Glycinate Complex) | 8-75 mcg (20 mcg) | Albion/Balchem |
| Iron (as Ferric Glycinate) | 2-30 mg (18 mg) | Albion/Balchem |
| Magnesium (as Magnesium Bisglycinate Chelate) | 10-200 mg (100 mg) | Albion/Balchem |
| Copper (as Copper Bisglycinate Chelate) | .1-2 mg (1 mg) | Albion/Balchem |
| Calcium (as Calcium Bisglycinate Chelate) | 50-600 mg (100 mg) | Albion/Balchem |
| Lutein (from marigolds: FloraGlo ®) | 10 mcg-10 mg (2 mg) | Kemin/DSM |
| Zeaxanthin (from marigolds: ZeaOne ®) | 10 mcg-10 mg (500 mcg) | Kemin/DSM |
| Fruit and vegetable powder blend: (Strawberry, Raspberry, Blueberry, Tart Cherry, Elderberry, Cranberry, Broccoli, Broccoli Sprouts, Tomato, Carrot, Spinach, Kale) | 20-200 mg (100 mg) | FutureCeuticals |

| Example 12 (Hair, Skin & Nails) Amount per serving: | | |
|---|---|---|
| Ingredient Name | Amount | Source |
| Vitamin C (from Acerola Cherry fruit extract) | 20-150 mg (20mg) | FutureCeuticals |
| D3 Vegan Cholecalciferol (VitaShine ®) | 5-50 mcg (10 mcg) | The GHT Companies |

Example 12 (Hair, Skin & Nails)
Amount per serving:

| Ingredient Name | Amount | Source |
|---|---|---|
| Vitamin B6 (as Pyridoxal-5-Phosphate) | 0.5-50 mg (2 mg) | Parchem |
| Quatrefolic ® - (6S)-5-methyltetrahydrofolate glucosamine salt | 50-800 mcg (200 mcg) | Gnosis |
| Vitamin B12 (as Methylcobalamin) | 0.5-15 mcg (4 mcg) | Parchem |
| Biotin (as d-Biotin) | 5-300 mcg (100 mcg) | DSM |
| Cranberry seed oil | 200-600mg (500 mg) | Nutrativa Global |
| Black Currant seed oil | 200-600mg (500 mg) | Connoils |
| Whole coffee fruit extract: Coffeeberry ® Cascara | 50-500 mg (50 mg) | FutureCeuticals |
| Fruit powder blend: (Strawberry, Raspberry, Blueberry, Tart Cherry, Elderberry, Cranberry) | 20-200 mg (50 mg) | FutureCeuticals |

Example 13 (B Complex)
Amount per serving:

| Ingredient Name | Amount | Source |
|---|---|---|
| Vitamin B6 (as Pyridoxal-5-) Phosphate | 0.5-50 mg (6 mg) | Parchem |
| Quatrefolic ® - (6S)-5-methyltetrahydrofolate glucosamine salt | 50-800 mcg (800 mcg) | Gnosis |
| Vitamin B12 (as Methylcobalamin) | 0.5-15 mcg (8 mcg) | Parchem |
| Fruit powder blend: (Strawberry, Raspberry, Blueberry, Tart Cherry, Elderberry, Cranberry) | 20-200 mg (50 mg) | FutureCeuticals |

Example 14 (Immune-Adult)
Amount per serving:

| Ingredient Name | Amount | Source |
|---|---|---|
| Vitamin C (from Acerola Cherry fruit extract) | 20-150 mg (80mg) | FutureCeuticals |
| Elderberry | 25-100 mg (50 mg) | FutureCeuticals |
| Black Currant | 5-50 mg (10 mg) | FutureCeuticals |
| Blackberry | 5-50 mg (10 mg) | FutureCeuticals |
| Blueberry | 5-50 mg (10 mg) | FutureCeuticals |
| Raspberry | 5-50 mg (10 mg) | FutureCeuticals |
| Pomegranate | 5-50 mg (10 mg) | FutureCeuticals |
| D3 Vegan Cholecalciferol (VitaShine ®) | 5-50 mcg (10 mcg) | The GHT Companies |
| Zinc Bisglycinate Chelate | 2-15 mg (6 mg) | Albion/Balchem |
| Vitamin B6 (as Pyridoxal-5-Phosphate) | .5-15 mg (1 mg) | Parchem |
| Quatrefolic ® - (6S)-5-methyltetrahydrofolate glucosamine salt | 50-800 mcg (100 mcg) | Gnosis |
| Methylcobalamin | 0.5-15 mcg (2 mcg) | Parchem |

Example 15 (Immune-Children)
Amount per serving:

| Ingredient Name | Amount | Source |
|---|---|---|
| Vitamin C (from Acerola Cherry fruit extract) | 20-150 mg (80mg) | FutureCeuticals |
| Elderberry | 25-100 mg (50 mg) | FutureCeuticals |
| Black Currant | 5-50 mg (10 mg) | FutureCeuticals |
| Blackberry | 5-50 mg (10 mg) | FutureCeuticals |
| Blueberry | 5-50 mg (10 mg) | FutureCeuticals |
| Raspberry | 5-50 mg (10 mg) | FutureCeuticals |
| Pomegranate | 5-50 mg (10 mg) | FutureCeuticals |
| D3 Vegan Cholecalciferol (VitaShine ®) | 5-50 mcg (5 mcg) | The GHT Companies |
| Zinc Bisglycinate Chelate | 2-15 mg (4 mg) | Albion/Balchem |
| Vitamin B6 (as Pyridoxal-5-Phosphate) | .5-15 mg (1 mg) | Parchem |
| Quatrefolic ® - (6S)-5-methyltetrahydrofolate glucosamine salt | 50-800 mcg (100 mcg) | Gnosis |
| Methylcobalamin | 0.5-15 mcg (1 mcg) | Parchem |

Example 16 (Calcium-Adult)
Amount per serving:

| Ingredient Name | Amount | Source |
|---|---|---|
| Calcium (as Calcium Bisglycinate Chelate) | 50-600 mg (200 mg) | Albion/Balchem |
| Calcium (as Calcium potassium phosphate citrate: Calci-K ®) | 50-600 mg (50 mg) | Albion/Balchem |
| D3 Vegan Choleciferol (VitaShine ®) | 5-50 mcg (5 mcg) | The GHT Companies |

-continued

Example 16 (Calcium-Adult)
Amount per serving:

| Ingredient Name | Amount | Source |
|---|---|---|
| Vitamin K2 (as Menaquinone-7: VitaMK7 ®) | 2-100 mcg (10 mcg) | Gnosis |
| Magnesium (as Magnesium Bisglycinate Chelate) | 10-400 mg (250 mg) | Albion/Balchem |
| Zinc (as Zinc Bisglycinate Chelate) | 2-15 mg (6 mg) | Albion/Balchem |
| Boron: (as Calcium Fructoborate: FruiteX-B ®) | .25 mcg-2 mg (200 mcg) | FutureCeuticals |
| Vitamin B6 (as Pyridoxal-5-Phosphate) | 0.5-50 mg (1 mg) | Parchem |
| Quatrefolic ® - (6S)-5-methyltetrahydrofolate glucosamine salt | 50-800 mcg (100 mcg) | Gnosis |
| Vitamin B12 (as Methylcobalamin) | 0.5-15 mcg (2 mcg) | Parchem |

Example 17 (Calcium-Children)
Amount per serving:

| Ingredient Name | Amount | Source |
|---|---|---|
| Calcium (as Calcium Bisglycinate Chelate) | 50-600 mg (125 mg) | Albion/Balchem |
| Calcium (as Calcium potassium phosphate citrate: Calci-K ®) | 50-600 mg (25 mg) | Albion/Balchem |
| D3 Vegan Cholecalciferol (VitaShine ®) | 5-50 mcg (5 mcg) | The GHT Companies |
| Vitamin K2 (as Menaquinone-7: VitaMK7 ®) | 2-100 mcg (5 mcg) | Gnosis |
| Magnesium (as Magnesium Bisglycinate Chelate) | 10-400 mg (150 mg) | Albion/Balchem |
| Zinc (as Zinc Bisglycinate Chelate) | 2-15 mg (4 mg) | Albion/Balchem |
| Boron: (as Calcium Fructoborate: FruiteX-B ®) | .25 mcg-2 mg (100 mcg) | FutureCeuticals |
| Vitamin B6 (as Pyridoxal-5-Phosphate) | 0.5-50 mg (1 mg) | Parchem |
| Quatrefolic ® - (6S)-5-methyltetrahydrofolate glucosamine salt | 50-800 mcg (100 mcg) | Gnosis |
| Vitamin B12 (as Methylcobalamin) | 0.5-15 mcg (1 mcg) | Parchem |

Example 18 (Brain & Eye Health-Adult)
Amount per serving:

| Ingredient Name | Amount | Source |
|---|---|---|
| Omega Oil (Chia Oil & DHA from Algae Oil) | 100-800 mg (275 mg) | DSM |
| Vitamin B6 (as Pyridoxal-5-Phosphate) | 0.5-50 mg (1 mg) | Parchem |
| Quatrefolic ® - (6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Choline (as Citicoline: Cognizin ®) | 2-600 mg (200 mg) | Kyowa Hakko USA |
| Lutein (from marigolds: FloraGlo ®) | 10 mcg-10 mg (4 mg) | Kemin/DSM |
| Zeaxanthin (from marigolds: ZeaOne ®) | 10 mcg-10 mg (1 mg) | Kemin/DSM |
| Lycopene (from tomato extract: redivivo ®) | 10 mcg-10 mg (1 mg) | Kemin/DSM |
| Fruit powder blend: (Strawberry, Raspberry, Blueberry, Tart Cherry, Elderberry, Cranberry) | 20-200 mg (50 mg) | FutureCeuticals |

Example 19 (Brain & Eye Health-Children)
Amount per serving:

| Ingredient Name | Amount | Source |
|---|---|---|
| Omega Oil (Chia Oil & DHA from Algae Oil) | 100-800 mg (275 mg) | DSM |
| Vitamin B6 (as Pyridoxal-5-Phosphate) | 0.5-50 mg (1 mg) | Parchem |
| Quatrefolic ® - (6S)-5-methyltetrahydrofolate glucosamine salt | 50-800 mcg (200 mcg) | Gnosis |
| Vitamin B12 (as Methylcobalamin) | 0.5-15 mcg (1 mcg) | Parchem |
| Choline (as Citicoline: Cognizin ®) | 2-600 mg (50 mg) | Kyowa Hakko USA |
| Lutein (from marigolds: FloraGlo ®) | 10 mcg-10 mg (2 mg) | Kemin/DSM |
| Zeaxanthin (from marigolds: ZeaOne ®) | 10 mcg-10 mg (500 mcg) | Kemin/DSM |
| Lycopene (from tomato extract: redivivo ®)) | 10 mcg-10 mg (500 mcg) | Kemin/DSM |
| Raspberry fruit powder | 25-100 mg (60 mg) | FutureCeuticals |

Example 20 (Vitamin D3-Adult)
Amount per serving:

| Ingredient Name | Amount | Source |
|---|---|---|
| D3 Vegan Cholecalciferol (VitaShine ®) | 5-50 mcg (25 mcg) | The GHT Companies |
| Vitamin K2 (as Menaquinone-7: VitaMK7 ®) | 2-100 mcg (5 mcg) | Gnosis |
| Vitamin B6 (as Pyridoxal-5-Phosphate) | 0.5-50 mg (1 mg) | Parchem |
| Quatrefolic ® - (6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Boron: (as Calcium Fructoborate: FruiteX-B ®) | .25 mcg-2 mg (200 mcg) | FutureCeuticals |
| Fruit powder blend: (Strawberry, Raspberry, Blueberry, Tart Cherry, Elderberry, Cranberry) | 20-200 mg (50 mg) | FutureCeuticals |

Example 21 (Vitamin D3-Children)
Amount per serving:

| Ingredient Name | Amount | Source |
|---|---|---|
| D3 Vegan Cholecalciferol (VitaShine ®) | 5-50 mcg (15 mcg) | The GHT Companies |
| Vitamin B6 (as Pyridoxal-5-Phosphate) | 0.5-50 mg (1 mg) | Parchem |
| Quatrefolic ® - (6S)-5-methyltetrahydrofolate glucosamine salt | 50-800 mcg (200 mcg) | Gnosis |
| Vitamin B12 (as Methylcobalamin) | 0.5-15 mcg (1 mcg) | Parchem |
| Fruit powder blend: (Strawberry, Raspberry, Blueberry, Tart Cherry, Elderberry, Cranberry) | 20-200 mg (25 mg) | FutureCeuticals |

Example 22 (Eye Health-Adult)
Amount per serving:

| Ingredient Name | Amount | Source |
|---|---|---|
| Lutein (from marigolds: FloraGlo ®) | 10 mcg-10 mg (8 mg) | Kemin/DSM |
| Zeaxanthin (from marigolds: ZeaOne ®) | .5-3 mg (2 mg) | Kemin/DSM |
| Vitamin B6 (as Pyridoxal-5-Phosphate) | 0.5-50 mg (1 mg) | Parchem |
| Quatrefolic ® - (6S)-5-methyltetrahydrofolate glucosamine salt | 50-800 mcg (100 mcg) | Gnosis |
| Vitamin B12 (as Methylcobalamin) | 0.5-15 mcg (2 mcg) | Parchem |
| Bilberry fruit powder | 25-100 mg (50 mg) | FutureCeuticals |
| Fruit powder blend: (Strawberry, Raspberry, Blueberry, Tart Cherry, Elderberry, Cranberry) | 20-200 mg (50 mg) | FutureCeuticals |

Example 23 (Caffeine)
Amount per serving:

| Ingredient Name | Amount | Source |
|---|---|---|
| Caffeine (from Organic Coffeeberry ® Energy organic coffee fruit caffeine) | 25-200 mg (50 mg) | FutureCeuticals |
| Vitamin B6 (as Pyridoxal-5-Phosphate) | 0.5-50 mg (1 mg) | Parchem |

Example 23 (Caffeine)
Amount per serving:

| Ingredient Name | Amount | Source |
| --- | --- | --- |
| Quatrefolic ® - (6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| L-Theanine (Suntheanine ®) | 25-200 mg (100 mg) | Taiyo International |

Example 24 (Iron-Adult)
Amount per serving:

| Ingredient Name | Amount | Source |
| --- | --- | --- |
| Vitamin C (from Acerola Cherry fruit extract) | 20-150 mg (30 mg) | FutureCeuticals |
| Iron (as Ferric Glycinate) | 2-30 mg (18 mg) | Albion/Balchem |
| Vitamin B6 (as Pyridoxal-5-Phosphate) | 0.5-50 mg (1 mg) | Parchem |
| Quatrefolic ®-(6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Fruit powder blend: (Strawberry, Raspberry, Blueberry, Tart Cherry, Elderberry, Cranberry) | 20-200 mg (50 mg) | FutureCeuticals |

Example 25 (Iron-Children)
Amount per serving:

| Ingredient Name | Amount | Source |
| --- | --- | --- |
| Vitamin C (from Acerola Cherry fruit extract) | 20-150 mg (20 mg) | FutureCeuticals |
| Iron (as Ferric Glycinate) | 2-30 mg (10 mg) | Albion/Balchem |
| Vitamin B6 (as Pyridoxal-5-Phosphate) | 0.5-50 mg (1 mg) | Parchem |
| Quatrefolic ®-(6S)-5-methyltetrahydrofolate glucosamine salt | 50-800 mcg (200 mcg) | Gnosis |
| Vitamin B12 (as Methylcobalamin) | 0.5-15 mcg (1 mcg) | Parchem |
| Fruit powder blend: (Strawberry, Raspberry, Blueberry, Tart Cherry, Elderberry, Cranberry) | 20-200 mg (50 mg) | FutureCeuticals |

Example 26 (Vitamin C)
Amount per serving:

| Ingredient Name | Amount | Source |
| --- | --- | --- |
| Vitamin C (from Acerola Cherry fruit extract) | 20-150 mg (150 mg) | FutureCeuticals |
| Quercetin | 50-200 mg (50 mg) | FutureCeuticals |
| Vitamin B6 (as Pyridoxal-5-Phosphate) | 0.5-50 mg (1 mg) | Parchem |
| Quatrefolic ®-(6S)-5-methyltetrahydrofolate glucosamine salt | 50-800 mcg (100 mcg) | Gnosis |
| Vitamin B12 (as Methylcobalamin) | 0.5-15 mcg (2 mcg) | Parchem |
| Fruit powder blend: (Strawberry, Raspberry, Blueberry, Tart Cherry, Elderberry, Cranberry) | 20-200 mg (50 mg) | FutureCeuticals |

Example 27 (Choline & Coffee Fruit Extract)
Amount per serving:

| Ingredient Name | Amount | Source |
| --- | --- | --- |
| Choline (as Citicoline: Cognizin ®) | 2-600 mg (250 mg) | Kyowa Hakko USA |
| Vitamin B6 (as Pyridoxal-5-Phosphate) | 0.5-50 mg (2 mg) | Parchem |
| Quatrefolic ®-(6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Whole coffee fruit extract: NeuroFactor ™ | 25-200 mg (100 mg) | FutureCeuticals |
| Fruit powder blend: (Strawberry, Raspberry, Blueberry, Tart Cherry, Elderberry, Cranberry) | 20-200 mg (50 mg) | FutureCeuticals |

Example 28 (Post Workout Recovery)
Amount per serving:

| Ingredient Name | Amount | Source |
| --- | --- | --- |
| Whole Montmorency tart cherry fruit powder: VitaCherry ® Sport | 300-500 mg (480 mg) | FutureCeuticals |
| Quercetin | 100-300 mg (250 mg) | FutureCeuticals |
| Vitamin C (from Acerola Cherry fruit extract) | 20-80 mg (40 mg) | FutureCeuticals |
| Whole coffee fruit extract: Coffeeberry ® Cascara | 50-500 mg (50 mg) | FutureCeuticals |
| Magnesium (as Magnesium Bisglycinate Chelate) | 10-200 mg (40 mg) | Albion/Balchem |
| Zinc (as Zinc Bisglycinate Chelate) | 2-15 mg (4 mg) | Albion/Balchem |
| Boron: (as Calcium Fructoborate: FruiteX-B ®) | .25 mcg-2 mg (500 mcg) | FutureCeuticals |
| Senonian Trace Minerals: elemin ® | 5-20 mg (10 mg) | FutureCeuticals |
| Vitamin B6 (as Pyridoxal-5-Phosphate) | 0.5-50 mg (2 mg) | Parchem |
| Quatrefolic ®-(6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Fruit powder blend: (Strawberry, Raspberry, Blueberry, Tart Cherry, Elderberry, Cranberry) | 20-200 mg (50 mg) | FutureCeuticals |

Example 29 (Sport Performance with Caffeine)
Amount per serving:

| Ingredient Name | Amount | Source |
|---|---|---|
| Caffeine (from Organic Coffeeberry ® Energy organic coffee fruit caffeine) | 25-200 mg (50 mg) | FutureCeuticals |
| Ancient peat and apple extract: elevATP ® | 100-200 mg (150 mg) | FutureCeuticals |
| Vitamin C (from Acerola Cherry fruit extract) | 20-80 mg (20 mg) | FutureCeuticals |
| Thiamin (as Cocarboxylase) | .25-5 mg (.25 mg) | Parchem |
| Niacin (as Inositol hexanicotinate and nicotinamide adenine dinucleotide) | 2-25 mg (4 mg) | Parchem |
| Riboflavin (as Riboflavin-5-Phosphate) | .25-5 mg (.25 mg) | Parchem |
| Pantothenic Acid (as Pantethine: Pantesin ®) | 1-15 mg (1 mg) | Kyowa Hakko USA |
| Vitamin B6 (as Pyridoxal-5-Phosphate) | 0.5-50 mg (2 mg) | Parchem |
| Quatrefolic ®-(6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Choline (as Citicoline: Cognizin ®) | 2-600 mg (20 mg) | Kyowa Hakko USA |
| Fruit powder blend: (Strawberry, Raspberry, Blueberry, Tart Cherry, Elderberry, Cranberry) | 20-200 mg (50 mg) | FutureCeuticals |

Example 30 (Sport Performance)
Amount per serving:

| Ingredient Name | Amount | Source |
|---|---|---|
| Ancient peat and apple extract: elevATP ® | 100-200 mg (150 mg) | FutureCeuticals |
| Vitamin C (from Acerola Cherry fruit extract) | 20-80 mg (20 mg) | FutureCeuticals |
| Thiamin (as Cocarboxylase) | .25-5 mg (.25 mg) | Parchem |
| Niacin (as Inositol hexanicotinate and nicotinamide adenine dinucleotide) | 2-25 mg (4 mg) | Parchem |
| Riboflavin (as Riboflavin-5-Phosphate) | .25-5 mg (.25 mg) | Parchem |
| Pantothenic Acid (as Pantethine: Pantesin ®) | 1-15 mg (1 mg) | Kyowa Hakko USA |
| Vitamin B6 (as Pyridoxal-5-Phosphate) | 0.5-50 mg (2 mg) | Parchem |
| Quatrefolic ®-(6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Choline (as Citicoline: Cognizin ®) | 2-600 mg (20 mg) | Kyowa Hakko USA |
| Fruit powder blend: (Strawberry, Raspberry, Blueberry, Tart Cherry, Elderberry, Cranberry) | 20-200 mg (50 mg) | FutureCeuticals |

Example 31 (Prenatal Multivitamin)
Amount per serving:

| Ingredient Name | Amount | Source |
|---|---|---|
| Vitamin C (as Ascorbic Acid) | 20-150 mg (60 mg) | Parchem |
| D3 Vegan Cholecalciferol (VitaShine ®) | 5-50 mcg (40 mcg) | The GHT Companies |
| Vitamin E (as d-alpha tocopherol succinate) | 5-100 IU (10 IU) | Marroquin Organics |
| Vitamin K2 (as Menaquinone-7: VitaMK7 ®) | 2-100 mcg (60 mcg) | Gnosis |
| Niacin (as Inositol hexanicotinate and nicotinamide adenine dinucleotide) | 2-25 mg (10 mg) | Parchem |
| Thiamin (as Cocarboxylase) | .25-5 mg (2 mg) | Parchem |
| Riboflavin (as Riboflavin-5-Phosphate) | .25-5 mg (1 mg) | Parchem |
| Pantothenic Acid (as Pantethine: Pantesin ®) | 2-15 mg (4 mg) | Kyowa Hakko USA |
| Vitamin B6 (as Pyridoxal-5-Phosphate) | 0.5-50 mg (6 mg) | Parchem |
| Quatrefolic ®-(6S)-5-methyltetrahydrofolate glucosamine salt | 50-800 mcg (800 mcg) | Gnosis |
| Vitamin B12 (as Methylcobalamin) | 0.5-15 mcg (8 mcg) | Parchem |
| Biotin (as d-Biotin) | 5-300 mcg (30 mcg) | DSM |
| Iodine (as Potassium Iodide) | 10-200 mcg (150 mcg) | Parchem |
| Choline (as Citicoline: Cognizin ®) | 2-600 mg (50 mg) | Kyowa Hakko USA |
| Boron: (as Calcium Fructoborate: FruiteX-B ®) | .25 mcg-2 mg (1 mg) | FutureCeuticals |
| Zinc (as Zinc Bisglycinate Chelate) | 2-15 mg (10 mg) | Albion/Balchem |
| Selenium (as Selenium Glycinate Complex) | 8-75 mcg (20 mcg) | Albion/Balchem |
| Iron (as Ferrous Bisglycinate Chelate: Ferrochel ®) | 2-30 mg (22 mg) | Albion/Balchem |
| Magnesium (as Magnesium Bisglycinate Chelate) | 10-200 mg (30 mg) | Albion/Balchem |
| Copper (as Copper Bisglycinate Chelate) | .1-2 mg (1 mg) | Albion/Balchem |
| Omega Oil (DHA from Algae Oil) | 100-800 mg (300 mg) | DSM |
| Fruit and vegetable powder blend: (Strawberry, Raspberry, Blueberry, Tart Cherry, Elderberry, Cranberry, Broccoli, Broccoli Sprouts, Tomato, Carrot, Spinach, Kale) | 20-200 mg (60 mg) | FutureCeuticals |

Example 32 (Children's Multivitamin)
Amount per serving:

| Ingredient Name | Amount | Source |
|---|---|---|
| Vitamin C (from Acerola Cherry fruit extract) | 20-150 mg (40 mg) | FutureCeuticals |
| D3 Vegan Cholecalciferol (VitaShine ®) | 5-50 mcg (10 mcg) | The GHT Companies |
| Vitamin E (as d-alpha tocopherol succinate) | 5-100 IU (6 IU) | Marroquin Organics |
| Vitamin K2 (as Menaquinone-7: VitaMK7 ®) | 2-100 mcg (5 mcg) | Gnosis |
| Niacin (as Inositol hexanicotinate and nicotinamide adenine dinucleotide) | 2-25 mg (5 mg) | Parchem |
| Thiamin (as Cocarboxylase) | .25-5 mg (.3 mg) | Parchem |

-continued

Example 32 (Children's Multivitamin)
Amount per serving:

| Ingredient Name | Amount | Source |
|---|---|---|
| Riboflavin (as Riboflavin-5-Phosphate) | .25-5 mg (.425 mg) | Parchem |
| Pantothenic Acid (as Pantethine: Pantesin ®) | 2-15 mg (2 mg) | Kyowa Hakko USA |
| Vitamin B6 (as Pyridoxal-5-Phosphate) | 0.5-50 mg (1 mg) | Parchem |
| Quatrefolic ®-(6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |
| Biotin (as d-Biotin) | 5-300 mcg (20 mcg) | DSM |
| Iodine (from Kelp) | 10-200 mcg (40 mcg) | Parchem |
| Choline (as Citicoline: Cognizin ®) | 2-600 mg (50 mg) | Kyowa Hakko USA |
| Boron: (as Calcium Fructoborate: FruiteX-B ®) | .25 mcg-2 mg (100 mcg) | FutureCeuticals |
| Zinc (as Zinc Bisglycinate Chelate) | 2-15 mg (4 mg) | Albion/Balchem |
| Iron (as Ferric Glycinate) | 2-30 mg (6 mg) | Albion/Balchem |
| Magnesium (as Magnesium Bisglycinate Chelate) | 10-200 mg (20 mg) | Albion/Balchem |
| Selenium (as Selenium Glycinate Complex) | 8-75 mcg (10 mcg) | Albion/Balchem |
| Lutein (from marigolds: FloraGlo ®) | 10 mcg-2 mg (50 mcg) | Kemin/DSM |
| Zeaxanthin (from marigolds: ZeaOne ®) | 10 mcg-2 mg (50 mcg) | Kemin/DSM |
| Inulin (from Jerusalem Artichoke Root | 5-30 mg (20 mg) | The Green Labs |
| Rose Hips: AuroraRed ®) | 5-50 mg (10 mg) | Denali BioTechnologies |
| Fruit Enzyme Blend | 5-20 mg (10 mg) | FutureCeuticals |
| Fruit and vegetable powder blend: Blueberry, Strawberry, Raspberry, Cherry, Elderberry, Cranberry, Blackberry, Bilberry, Black Currant, Pomegranate, Broccoli, Broccoli Sprouts, Tomato, Carrot, Spinach, Kale, Cauliflower, Brussels Sprouts, Beet, Orange, Collard Greens, Lemon, Lime, Apple, Grape, Grape Seed, Pineapple, Goji Berry, Banana, Mango, Kiwi, Onion, Cucumber, Watermelon, Aronia Berry, Acai Berry, Cabbage, Asparagus, Pear, Red bell pepper, Green bell pepper, Plum, Parsley, Sweet potato, Radish sprouts, Okra, Pumpkin | 20-200 mg (200 mg) | FutureCeuticals |

Example 33 (Immune)
Amount per serving:

| Ingredient Name | Amount | Source |
|---|---|---|
| Vitamin C (from Acerola Cherry fruit extract) | 20-80 mg (40 mg) | FutureCeuticals |
| Beta-Glucan from Algae: | 50-300 mg | Kemin/DSM |

-continued

Example 33 (Immune)
Amount per serving:

| Ingredient Name | Amount | Source |
|---|---|---|
| BetaVia ® | (200 mg) | |
| Vitamin B6 (as Pyridoxal-5-Phosphate) | .5-15 mg (1 mg) | Parchem |
| Quatrefolic ®-(6S)-5-methyltetrahydrofolate glucosamine salt | 50-800 mcg (100 mcg) | Gnosis |
| Methylcobalamin | 0.5-15 mcg (2 mcg) | Parchem |
| Fruit powder blend: (Strawberry, Raspberry, Blueberry, Tart Cherry, Elderberry, Cranberry) | 20-200 mg (50 mg) | FutureCeuticals |

Example 34 (Trace Minerals)
Amount per serving:

| Ingredient Name | Amount | Source |
|---|---|---|
| Senonian Trace Minerals: elemin ® | 5-20 mg (10 mg) | FutureCeuticals |
| Vitamin B6 (as Pyridoxal-5-Phosphate) | .5-15 mg (1 mg) | Parchem |
| Quatrefolic ®-(6S)-5-methyltetrahydrofolate glucosamine salt | 50-800 mcg (100 mcg) | Gnosis |
| Methylcobalamin | 0.5-15 mcg (2 mcg) | Parchem |
| Fruit powder blend: (Strawberry, Raspberry, Blueberry, Tart Cherry, Elderberry, Cranberry) | 20-200 mg (50 mg) | FutureCeuticals |

Example 35 (Caffeine)
Amount per serving:

| Ingredient Name | Amount | Source |
|---|---|---|
| Caffeine (from Organic Coffeeberry ® Energy organic coffee fruit caffeine) | 25-200 mg (90 mg) | FutureCeuticals |
| Vitamin B6 (as Pyridoxal-5-Phosphate) | 0.5-50 mg (1 mg) | Parchem |
| Quatrefolic ®-(6S)-5-methyltetrahydrofolate glucosamine salt | 50-800 mcg (200 mcg) | Gnosis |
| Vitamin B12 (as Methylcobalamin) | 0.5-15 mcg (2 mcg) | Parchem |

Example 36 (Vitamin A from Fruits & Vegetables)
Amount per serving:

| Ingredient Name | Amount | Source |
|---|---|---|
| Apricot powder | 20-150 mg (100 mg) | FutureCeuticals |
| Broccoli powder | 20-150 mg (100 mg) | FutureCeuticals |
| Carrot powder | 20-150 mg (100 mg) | FutureCeuticals |
| Kale powder | 20-150 mg (100 mg) | FutureCeuticals |
| Mango powder | 20-150 mg (100 mg) | FutureCeuticals |
| Pumpkin powder | 20-150 mg (100 mg) | FutureCeuticals |

Example 36 (Vitamin A from Fruits & Vegetables)
Amount per serving:

| Ingredient Name | Amount | Source |
|---|---|---|
| Red bell pepper powder | 20-150 mg (100 mg) | FutureCeuticals |
| Spinach powder | 20-150 mg (100 mg) | FutureCeuticals |
| Sweet potato powder | 20-150 mg (100 mg) | FutureCeuticals |
| Tomato powder | 20-150 mg (100 mg) | FutureCeuticals |
| Vitamin B6 (as Pyridoxal-5-Phosphate) | .5-15 mg (1 mg) | Parchem |
| Quatrefolic ®-(6S)-5-methyltetrahydrofolate glucosamine salt | 50-800 mcg (100 mcg) | Gnosis |
| Methylcobalamin | 0.5-15 mcg (2 mcg) | Parchem |

Example 37 (Super B Complex)
Amount per serving:

| Ingredient Name | Amount | Source |
|---|---|---|
| Vitamin B6 (as Pyridoxal-5-Phosphate) | 0.5-50 mg (6 mg) | Parchem |
| Quatrefolic ®-(6S)-5-methyltetrahydrofolate glucosamine salt | 50-800 mcg (800 mcg) | Gnosis |
| Vitamin B12 (as Methylcobalamin) | 0.5-15 mcg (8 mcg) | Parchem |
| Niacin (as Inositol hexanicotinate and nicotinamide adenine dinucleotide) | 2-25 mg (10 mg) | Parchem |
| Thiamin (as Cocarboxylase) | .25-5 mg (.5 mg) | Parchem |
| Riboflavin (as Riboflavin-5-Phosphate) | .25-5 mg (.5 mg) | Parchem |
| Pantothenic Acid (as Pantethine: Pantesing | 2-15 mg (2.5 mg) | Kyowa Hakko USA |
| Biotin (as d-Biotin) | 5-300 mcg (20 mcg) | DSM |
| Vitamin C (from Acerola Cherry fruit extract) | 20-150 mg (20 mg) | FutureCeuticals |
| Choline (as Citicoline: Cognizin ®) | 2-600 mg (20 mg) | Kyowa Hakko USA |
| Fruit powder blend: (Strawberry, Raspberry, Blueberry, Tart Cherry, Elderberry, Cranberry) | 20-200 mg (50 mg) | FutureCeuticals |

Example 38 (Healthy Veins)
Amount per serving:

| Ingredient Name | Amount | Source |
|---|---|---|
| Vitamin C (from Acerola Cherry fruit extract) | 20-150 mg (50 mg) | FutureCeuticals |
| Vitamin B6 (as Pyridoxal-5-Phosphate) | 0.5-50 mg (6 mg) | Parchem |
| Quatrefolic ®-(6S)-5-methyltetrahydrofolate glucosamine salt | 50-800 mcg (800 mcg) | Gnosis |
| Vitamin B12 (as Methylcobalamin) | 0.5-15 mcg (8 mcg) | Parchem |
| Resveratrol powder | 30-60 mg (50 mg) | FutureCeuticals |
| Grape seed extract: VitaGrape™ | 50-100 mg (50 mg) | FutureCeuticals |
| Bilberry fruit powder | 25-100 mg (50 mg) | FutureCeuticals |
| Quercetin | 50-200 mg (100 mg) | FutureCeuticals |
| Fruit powder blend: (Strawberry, Raspberry, Blueberry, Tart Cherry, Elderberry, Cranberry) | 20-200 mg (50 mg) | FutureCeuticals |

It will be understood that Examples 4-7 may comprise standalone vitamin supplement compositions and/or be incorporated into Examples 1-3. Moreover, Examples 1-38 may comprise derivatives and/or any hybrid of one another. Examples 1-38 may also be combined, in whole or in part, to express a new and/or modified example. Preferred amounts for one or more of the above-identified Examples are provided therewithin in parentheses.

It will be further understood that any reference to compounds disclosed herein includes salts and/or solvates of the same.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A vitamin supplement composition that comprises a complex with enhanced bioavailability, comprising:
    a vitamin B complex, wherein the vitamin B complex comprises:
        a first vitamin, wherein the first vitamin comprises a form of vitamin $B_6$;
        a second vitamin, wherein the second vitamin comprises the structure of formula IV or nutraceutically acceptable salts or solvates thereof:

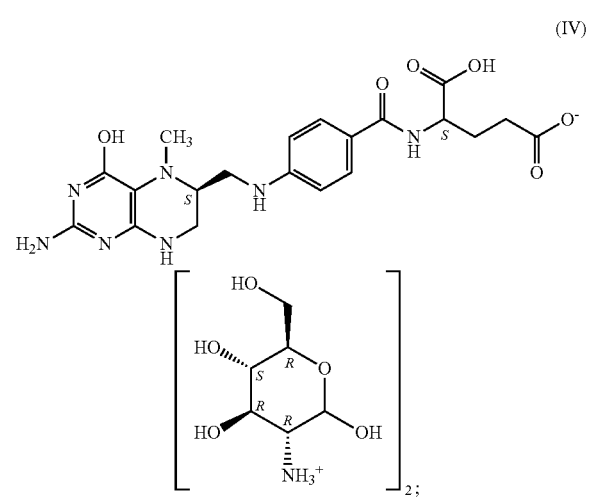

(IV)

and
    a third vitamin, wherein the third vitamin comprises a form of vitamin $B_{12}$.

2. The vitamin supplement composition according to claim 1, wherein the first vitamin comprises the structure of formula I or nutraceutically acceptable salts or solvates thereof:

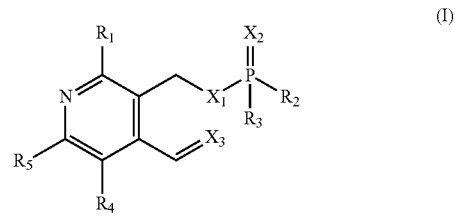

(I)

wherein $R_1$-$R_6$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s);
wherein at least three of $R_1$-$R_5$ comprise OH; and
wherein $X_1$-$X_3$ are each independently selected from the group consisting of N—$R_6$; O; and S.

3. The vitamin supplement composition according to claim 1, wherein the first vitamin comprises the structure of formula II or nutraceutically acceptable salts or solvates thereof:

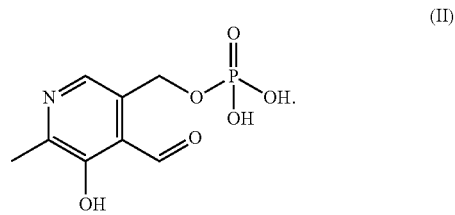 [SMILES: Cc1ncc(COP(=O)(O)O)c(C=O)c1O]

(II)

4. The vitamin supplement composition according to claim 1, wherein the second vitamin comprises the structure of formula III or nutraceutically acceptable salts or solvates thereof:

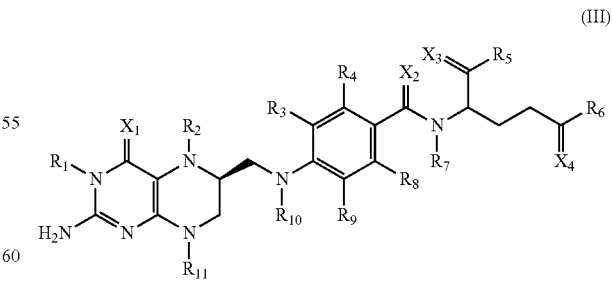

(III)

wherein $R_1$-$R_{12}$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); and wherein $X_1$-$X_4$ are each independently selected from the group consisting of N—$R_{12}$; O; and S.

5. The vitamin supplement composition according to claim 1, wherein the third vitamin comprises the structure of formula V or nutraceutically acceptable salts or solvates thereof:

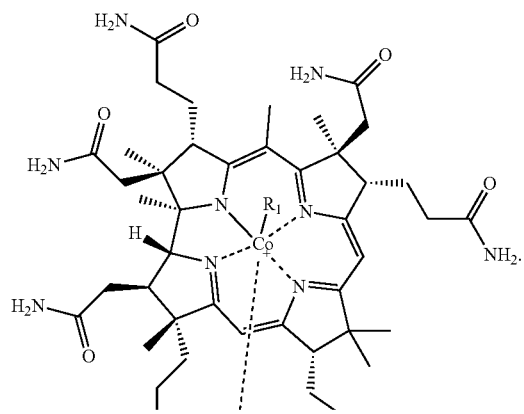

(V)

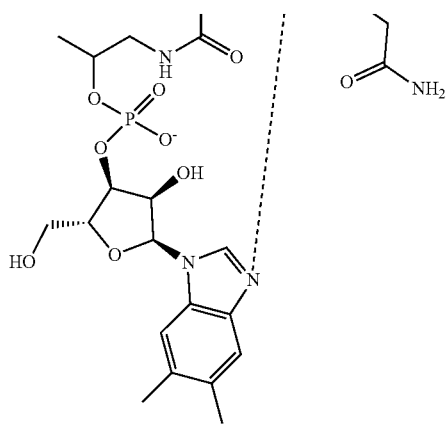

wherein $R_1$ is selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s).

6. The vitamin supplement composition according to claim 1, wherein the third vitamin comprises the structure of formula VI or nutraceutically acceptable salts or solvates thereof:

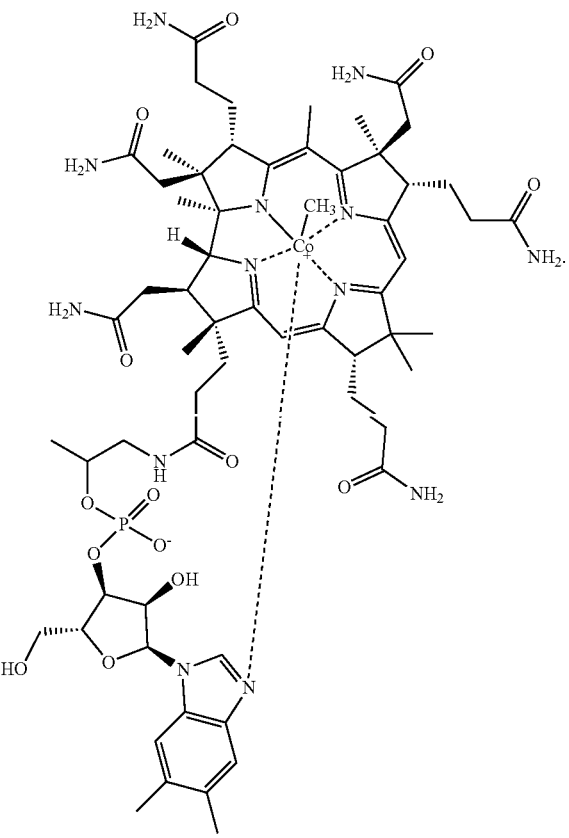

(VI)

7. The vitamin supplement composition according to claim 1, wherein the weight ratio of the first vitamin to the second vitamin to the third vitamin ranges from approximately 300:50:1 to approximately 30:50:1 by weight of the total vitamin B complex.

8. The vitamin supplement composition according to claim 1, wherein the weight ratio of the first vitamin to the second vitamin to the third vitamin is approximately 200:55:1 by weight of the total vitamin B complex.

9. The vitamin supplement composition according to claim 1, further comprising at least one of vitamin A, vitamin C, vitamin D, vitamin E, vitamin K, thiamin, riboflavin, niacin, biotin, pantothenic acid, calcium, iron, iodine, magnesium, zinc, selenium, copper, manganese, chromium, molybdenum, choline, boron, lutein, lycopene, inositol, fruit and/or vegetable blend, and combinations thereof.

10. The vitamin supplement composition according to claim 1, further comprising at least one of sweeteners, beeswax, carnuba wax, flavors, emulsifiers, preservatives, colors, glaze, syrups, silica, malic acid, citric acid, magnesium stearate, cellulose, microcrystalline cellulose, croscarmellose sodium, silicon dioxide, maltodextrin, sunflower lecithin, guar gum, sunflower oil, coconut oil, vegetable cellulose, stearic acid, vegetable magnesium stearate, pectin, sodium citrate, dicalcium phosphate, and combinations thereof.

11. The vitamin supplement composition according to claim 1, further comprising a vitamin/mineral selected from the group consisting of vitamin A, thiamin, riboflavin, niacin, pantothenic acid, biotin, vitamin C, choline, vitamin D, vitamin E, vitamin K, calcium, chloride, chromium, copper, fluoride, iodine, iron, magnesium, manganese, molybdenum, nickel, phosphorus, potassium, silicon, selenium, sodium, sulfur, tin, vanadium, zinc, and combinations thereof.

12. The vitamin supplement composition according to claim 1, further comprising an amino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, L-valine, and combinations thereof.

13. A vitamin supplement composition having a vitamin complex with enhanced bioavailability, comprising:

a vitamin B complex, wherein the vitamin B complex comprises:

a first vitamin, wherein the first vitamin comprises [(4-formyl-5-hydroxy-6-methylpyridin-3-yl) methoxy]phosphonic acid;

a second vitamin, wherein the second vitamin comprises the structure of formula IV or nutraceutically acceptable salts or solvates thereof:

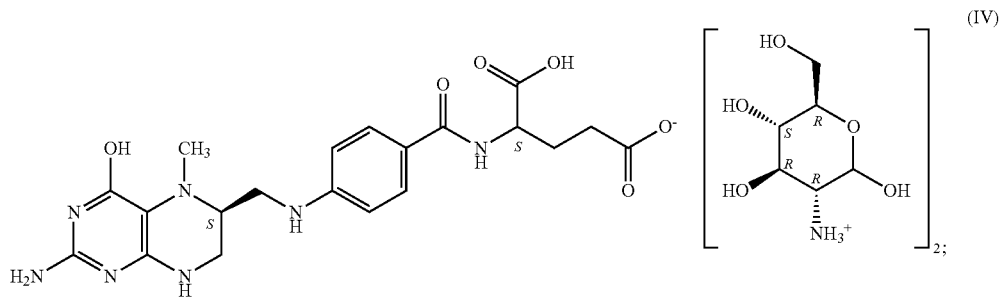

and a third vitamin, wherein the third vitamin comprises methylcobalamin.

14. A method for treating an individual, comprising the steps of:

orally administering a vitamin B complex, wherein the vitamin B complex comprises:

a first vitamin, wherein the first vitamin comprises a form of vitamin $B_6$;

a second vitamin, wherein the second vitamin comprises the structure of formula IV or nutraceutically acceptable salts or solvates thereof:

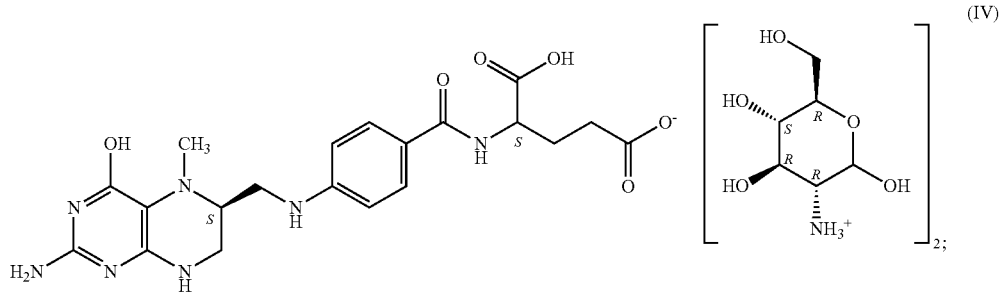

a third vitamin, wherein the third vitamin comprises a form of vitamin $B_{12}$; and wherein at least two of the first vitamin, the second vitamin, and the third vitamin cooperate synergistically to enhance bioavailability of the same.

* * * * *